United States Patent [19]
Reitz et al.

[11] Patent Number: 5,817,668
[45] Date of Patent: Oct. 6, 1998

[54] S-HETEROATOM CONTAINING ALKYL SUBSTITUTED-3-OXO-PYRIDO[1,2-A] BENZIMIDOZOLE-4-CARBOXAMIDE DERIVATIVES USEFUL IN TREATING CENTRAL NERVOUS SYSTEM DISORDERS

[75] Inventors: Allen B. Reitz, Lansdale; Alfonzo D. Jordan, Horsham, both of Pa.; Pauline J. Sanfilippo, Flemington, N.J.; Anna Vavouyios-Smith, Austin, Tex.

[73] Assignee: Ortho Pharmaceutical Corporation, Raritan, N.J.

[21] Appl. No.: 943,578

[22] Filed: Oct. 3, 1997

Related U.S. Application Data

[60] Provisional application No. 60/027,511, Oct. 7, 1996.
[51] Int. Cl.$^6$ ...................... A61K 31/435; A61K 31/535; C07D 471/04
[52] U.S. Cl. ...................... 514/292; 514/233.2; 514/253; 544/126; 544/361; 546/86
[58] Field of Search ............................... 546/86; 544/126, 544/361; 514/233.2, 253, 292

[56] References Cited

U.S. PATENT DOCUMENTS 5,639,760  6/1997  Maryanoff et al. ..................... 514/292

*Primary Examiner*—Johann Richter
*Assistant Examiner*—Laura L. Stockton
*Attorney, Agent, or Firm*—Ralph R. Palo

[57] ABSTRACT

A compound of the general formula 1;

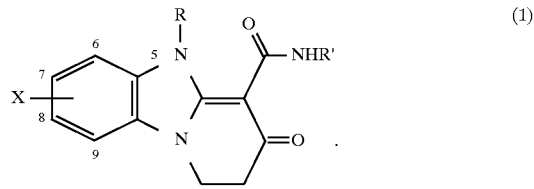

is disclosed as useful in treating disorders of the central nervous system. Pharmaceutical compositions and methods of treatment are also disclosed.

21 Claims, No Drawings

S-HETEROATOM CONTAINING ALKYL SUBSTITUTED-3-OXO-PYRIDO[1,2-A] BENZIMIDOZOLE-4-CARBOXAMIDE DERIVATIVES USEFUL IN TREATING CENTRAL NERVOUS SYSTEM DISORDERS

This application is based on provisional application Ser. No. 60/027,511 filed Oct. 7, 1996.

BACKGROUND OF THE INVENTION

The gamma-aminobutyric acid-A receptor (GABA-A receptor) is the most abundant inhibitory receptor in the brain of mammals. It is comprised of a heteropolymeric structure that forms a chloride ion channel, and bears multiple recognition sites for the binding of modulatory molecules. The binding of GABA to its specific recognition site on the GABA-A receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA-A receptor (Smith and Olsen, *Trends Pharm. Sci.*, 1995, 16, 162; Stephenson, *Biochem. J.*, 1995, 310, 1). The so-called benzodiazepine (BZD) receptor is a site for such allosteric modulators on the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. *J. Med. Chem.* 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. *Arzneim.-Forsch./Drug Res.* 1992, 42 (2a), 211; Haefely, W. et al., *Advances in Drug Research*, Academic Press, vol. 14, 1985, pp. 165–322; Skolnick, P. et al., *GABA and Benzodiazepine Receptors*, Squires, R., Ed., 1987, pp. 99–102 and references cited therein.)

The benzodiazepines are a class of compounds which bind to the BZD receptor with high affinity. Most of the drugs in use are agonist-type ligands for the receptor. Such compounds are generally useful for their anticonvulsant, anxiolytic, sedative, and muscle relaxant effects. Antagonists of the BZD binding site are useful for the treatment of benzodiazepine drug overdose and inverse agonists are useful in managing alcoholism.

The present invention is concerned with novel compositions of matter and their use. Compounds having some structural similarity to those of the present invention are described in Rida, S. M. et al. *J. Het. Chem.* 1988, 25, 1087; Soliman, F. S. G. et al. *Arch. Pharm.* 1984, 317, 951; Volovenko, Y. M. et al. U.S.S.R. Patent SU 1027166 (*Chem Abs.* 99(25) 212524t); Ohta, S. et al. *Heterocycles* 1991, 32, 1923; Ohta, S. et al. *Chem. Pharm. Bull.* 1991, 39, 2787. In addition, related compounds are disclosed in U.S. application Ser. No. 08/387,720, assigned to the assignee of the present invention and in applications bearing applicants' docket numbers MCN-529.

DISCLOSURE OF THE INVENTION

The present invention is directed to compounds of the following formula 1:

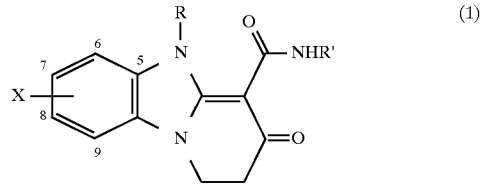

wherein R, Ar, and X are as defined hereinafter. The compounds of formula 1 are useful in treating central nervous system disorders. The compounds are ligands for the BZD binding site on GABA-A receptors, and are thus useful as muscle relaxants, hypnotics/sedatives including sleep-aids, anxiolytics, anticonvulsants/antiepileptics, anti-inebriants, and antidotes for drug overdose (particularly benzodiazepine overdoses).

The present invention also comprises pharmaceutical compositions containing one or more of the compounds of formula 1 and methods for the treatment of disorders to the central nervous system including convulsions such as epileptic seizures, anxiety, muscular spasms, sleep disorders, and benzodiazepine overdoses employing a compound of formula 1.

DETAILED DESCRIPTION OF THE INVENTION

More particularly, the present invention is directed to compounds of the following formula 1:

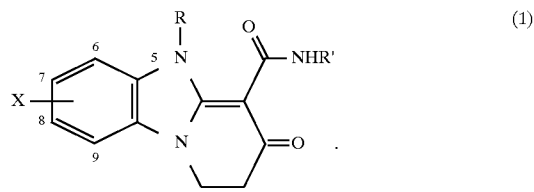

X is independently selected from any of hydrogen, alkyl ($C_1$–$C_8$), branched alkyl($C_3$–$C_8$), halogen, perfluoro ($C_1$–$C_4$ alkyl), hydroxy, $C_1$–$C_4$ alkoxy, di($C_1$–$C_4$ alkyl) amino, amino alkylamino, $C_1$–$C_4$ alkoxycarbonyl, or $C_1$–$C_4$ alkylthio. There may be up to four independent X substituents on the phenyl. More preferably, X is independently selected from any of $C_1$–$C_4$ alkoxy, hydrogen, halogen, or alkyl($C_1$–$C_8$). Preferably, there is only one X substituent other than hydrogen. Most preferably, X is 7-F.

R is selected from any of $(CH_2)_n NR_2 R_3$, where n=1–4, $R_2$ and $R_3$ may be the same or different and are selected from any of hydrogen, alkyl($C_1$–$C_{12}$), perfluoro($C_1$–$C_4$ alkyl), cycloalkyl($C_3$–$C_{10}$), alkoxy($C_1$–$C_8$), phenyl or substituted phenyl, where the phenyl substituents are selected from any of alkyl($C_1$–$C_8$), branched alky ($C_3$–$C_8$), halogen, perfluoro($C_1$–$C_4$ alkyl), hydroxy, $C_1$–$C_4$ alkoxy, di($C_1$–$C_4$ alkyl)amino, $C_{1-C4}$ alkoxycarbonyl or $C_1$–$C_4$ alkylthio; or $R_2$ and $R_3$ may be taken together with the nitrogen to form a cycloalkylamine ($C_3$–$C_{10}$), substituted piperazine, substituted morpholine, amidine, substituted amidine or guanidine wherein the substituted piperazine, morpholine and amidine may be substituted with up to three substituents independently selected from any of $C_1$–$C_4$ alkyl or aralkyl($C_1$–$C_4$) or lower alkoxy; or ($CH_2$)$_n$N($R_4$)C(O)$R_5$, where n=1–4, $R_4$ is selected from any of hydrogen, alkyl($C_1$–$C_{12}$) or cycloalkyl($C_3$–$C_{10}$), $R_5$ is selected from any of alkyl($C_1$–$C_{12}$), perfluoro ($C_1$–$C_4$ alkyl), cycloalkyl($C_3$–$C_{10}$), alkoxy($C_1$–$C_8$), phenyl or substituted phenyl, where the phenyl substituents are selected from any of alkyl($C_1$–$C_8$), branched alkyl($C_3$–$C_8$), halogen, perfluoro(lower alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; $R_5$ may also be a heterocycle selected from any of pyridine, pyridine-N-oxide, thiazole, thiophene, indole, benzothiophene, pyridazine, pyrimidine, indole, benzofuran, isoquinoline, or oxazole, which heterocycle may be substituted with one or more substituents which are independently selected from any of halogen, nitro, lower amido, lower alkoxy, di(lower alkyl) amino, carboxy, lower alkoxycarbonyl, or lower alkyl; N($R_4$)C(O)$R_5$ may be a substituted carbamate or urea wherein the substituents are selected from any of alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or ($CH_2$)$_n$N($R_4$)S(O)$_2$$R_6$, where n=1–4, $R_4$ is previously defined, $R_6$ is selected from any of alkyl($C_1$–$C_{12}$), perfluoro($C_1$4 $C_4$ alkyl), cycloalkyl($C_3$–$C_{10}$), phenyl and substituted phenyl, where the phenyl substituents are selected from any of alkyl($C_1$–$C_8$), branched alkyl ($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; $R_6$ may also be a heterocycle selected from pyridine, pyridine-N-oxide, thiazole, thiophene, indole, benzothiophene, pyridazine, pyrimidine, indole, benzofuran, isoquinoline, or oxazole which heterocycle may be substituted with one or more substituents which are independently selected from any of halogen, nitro, $C_1$–$C_4$ amido, $C_1$–$C_4$ alkoxy, di($C_1$–$C_4$ alkyl)amino, carboxy, $C_1$–$C_4$ alkoxycarbonyl, or $C_1$–$C_4$ alkyl; or ($CH_2$)$_n$O$R_7$, where n=1–4, $R_7$ is selected from any of hydrogen, alkyl($C_1$–$C_{12}$), cycloalkyl($C_3$–$C_{10}$), phenyl or substituted phenyl, where the phenyl substituents are selected from any of alkyl($C_1$–$C_8$), branched alkyl ($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or $C_1$–$C_4$ acyl($C_1$–$C_4$) or aracyl($C_7$–$C_{10}$); or C(O)NH($C_1$–$C_4$ alkyl) or C(O)NH (aryl); or ($CH_2$)$_n$CR$_8$R$_9$OR$_{10}$, where n=1–3 and $R_8$ and $R_9$ are either one or both OR$_{11}$; if both $R_8$ or $R_9$ are not OR$_{11}$, then the non-OR$_{11}$ substituent is either H or lower alkyl, $R_{10}$ and $R_{11}$ are lower alkyl and can same or different and taken together to form a ring of 4–7 members; or ($CH_2$)$_n$CN, where n=1–3; or ($CH_2$)nS(O)$_m$$R_7$, where n=1–4 and m=0–2, $R_7$ is selected from any of hydrogen, alkyl($C_1$–$C_{12}$), cycloalkyl ($C_3$–$C_{10}$), phenyl or substituted phenyl, where the phenyl substituents are selected from any of alkyl ($C_1$–$C_8$), branched alkyl($C_3$–$C_8$), halogen, perfluoro (lower alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; or ($CH_2$)nC(O)NR$_4$R$_{12}$, where n=1–3, $R_4$ is as previously defined, and $R_{12}$ is defined as $R_4$ except that $R_4$ and $R_{12}$ do not need to be the same in any particular compound; or ($CH_2$)$_n$C(O)OR$_{13}$ where n=1–4 and $R_{13}$ is hydrogen or lower alkyl($C_1$–$C_6$).

More preferably, R is ($CH_2$)nOR$_7$, where n=1–4, $R_7$ is selected from any of hydrogen, alkyl($C_1$–$C_{12}$), cycloalkyl ($C_3$–$C_{10}$), phenyl or substituted phenyl, where the phenyl substituents are selected from any of alkyl($C_1$–$C_8$), branched alkyl($C_3$–$C_8$), halogen, perfluoro(lower alkyl), hydroxy, $C_1$–$C_4$ alkoxy, di(lower alkyl)amino, lower alkoxycarbonyl or $C_1$–$C_4$ alkylthio. Most preferably, R is any of 2-(methoxy)ethyl, 2-(ethoxy)ethyl, or ethoxymethyl.

The substituted phenyls described in connection with R herein above may contain up to 5 substituents, but preferably up to 4 substituents.

R' is selected from any of phenyl, substituted phenyl, where the phenyl substituents are selected from any of alkyl($C_1$–$C_8$), halogens, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; a heterocycle selected from any of pyridine, pyridine-N-oxide, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole; a substituted heterocycle where there are one or more substituents which are independently selected from any of halogen, perfluoro ($C_1$–$C_4$)alkyl, nitro, $C_1$–$C_4$ alkylthio, $C_1$–$C_4$ alkoxy, $C_1$–$C_4$ alkyl, di($C_1$–$C_4$ alkyl)amino, carboxy or $C_1$–$C_4$ alkoxycarbonyl; or a cycloalkyl ring comprising 3–8 carbon atoms. More preferably, R' is substituted phenyl. The substituted phenyl may contain up to 5 substituents, but preferably up to 2 substituents. Most preferably, R' is either of 2,4-diFPh or 2-FPh or 2-F-4-(methoxy)Ph.

As used herein unless otherwise noted, alkyl and alkoxy whether used alone or as part of a substituent group, include straight and branched chains. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. Unless otherwise noted, "lower" when used with alkyl and alkoxy means a carbon chain composition of 1–4 carbon atoms. Of course, if the alkyl or alkoxy substituent is branched there must be at least 3 carbons.

The term "aryl" as used herein alone or in combination with other terms indicates aromatic hydrocarbon groups such as phenyl or naphthyl. The term "aralkyl" means a radical containing a lower alkyl group substituted with an aryl radical. With reference to substituents, the term independently means that when more than one of such substituent is possible, such substituents may be the same or different from each other.

The particularly preferred compounds according to the present invention, as a result of their superior side effects profile and excellent potency, are:

Cmpd. 172

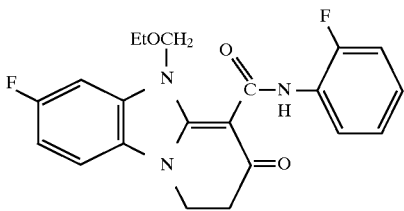

5-Ethoxymethyl-7-fluoro-4-
[N-(2-fluorophenyl)carboxamido]-
1,2-dihydro-3-oxopyrido[1,2-a]
benzimidazole Cmpd. 163

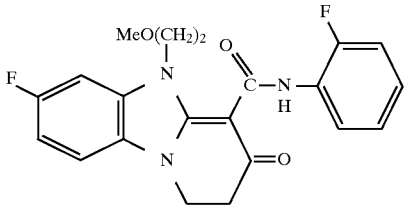

5-Methoxyethyl-7-fluoro-4-
[N-(2-fluorophenyl)carboxamido]-
1,2-dihydro-3-oxopyrido[1,2-a]
benzimidazole Cmpd. 161

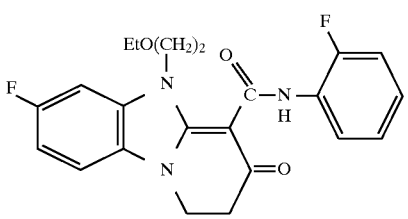

5-Ethoxyethyl-7-fluoro-4-[N-(2-fluoro-
phenyl)carboxamido]-1,2-dihydro-
3-oxopyrido[1,2-a]benzimidazole Cmpd. 137

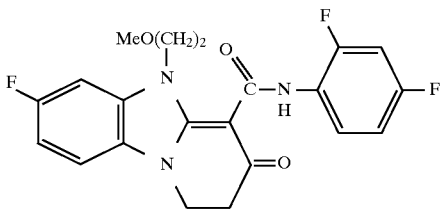

5-Methoxyethyl-7-fluoro-4-[N-(2,4-
difluorophenyl)carboxamido]-1,2-
dihydro-3-oxopyrido[1,2-a]
benzimidazole The most preferred compounds are:
Cmpd. 172

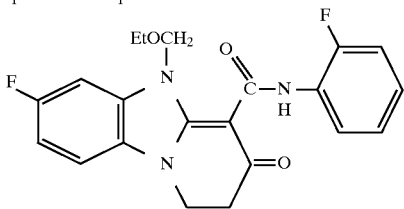

5-Ethoxymethyl-7-fluoro-4-
[N-(2-fluorophenyl)carboxamido]-
1,2-dihydro-3-oxopyrido[1,2-a]
benzimidazole and one of its primary metabolites:
Cmpd. 99

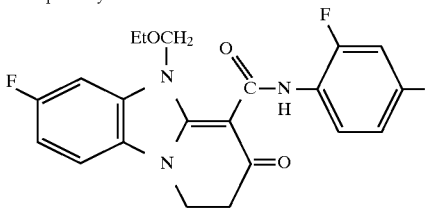

5-Ethoxyethyl-7-fluoro-4-
[N-(2-fluoro-4-hydroxyphenyl)-
carboxamido]-1,2-dihydro-3-
oxopyrido[1,2-a]benzimidazole When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. Such salts can are made by reacting the free base of compounds of formula 1 with the acid and isolating salts.

Hydrates and other solvates of the compound of formula 1 are also included within the scope of this invention and included within the definition of formula 1.

The compounds of formula 1 are prepared as outlined in Schemes 1–7.

Scheme 1

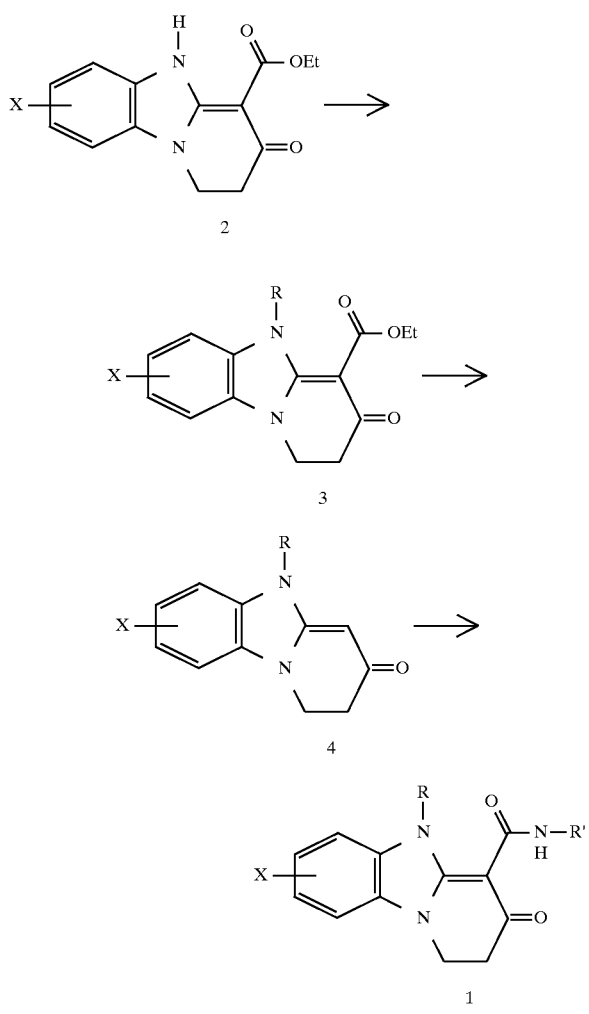

The pyridobenzimidazole ester derivative 2 is manufactured according to the following Scheme 1a.

Scheme 1a

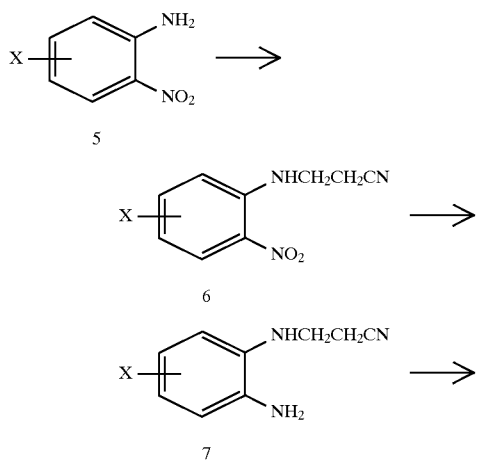

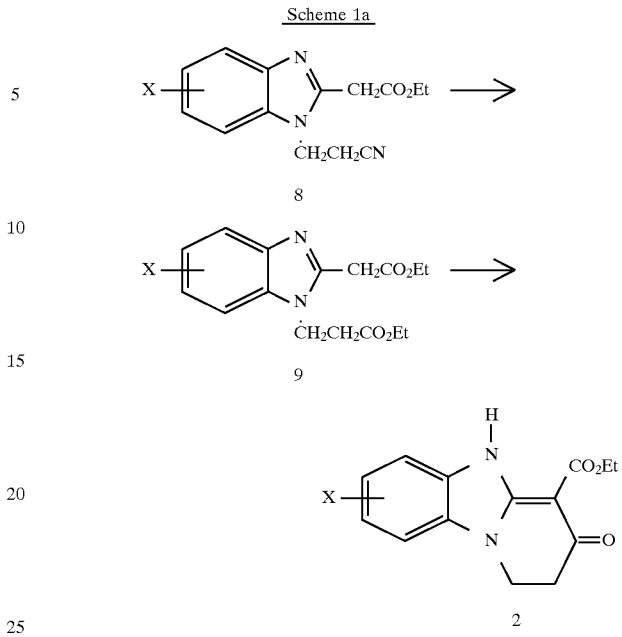

More specifically, the substituted nitroaniline derivative 5, commercially available (e.g.; Aldrich Chemical Co.) or prepared by standard methods known in the art, is treated with a mixture of acrylonitrile and a suitable base such as Triton B (N-benzyltrimethylammonium hydroxide) in an appropriate solvent such as dioxane at room temperature for 1–4 days to give the desired nitrile derivative 6. The nitro group of the nitrile derivative 6 is reduced to give the amino derivative 7 by treatment of said derivative with a suitable reduction catalyst such as Pd/C in an appropriate solvent such as ethyl acetate under a hydrogen atmosphere of about 50–60 psig for about 3–12 h. The benzimidazole derivative 8 is prepared by heating the amino derivative 7 with ethyl ethoxycarbonylacetimidate.HCl in a suitable solvent such as EtOH for about 4–24 h. Treatment of said benzimidazole derivative with an anhydrous acid such as HCl(g) in an appropriate solvent such as EtOH at reflux for about 4–24 h gives the diester derivative 9. The diester is treated with a suitable base such as sodium ethoxide in an appropriate solvent such as EtOH for about 12–24 h at room temperature followed by treatment with ethanolic HCl to give pyridobenzimidazole 1.

As shown in Scheme 1, the alkylated pyridobenzimidazole ester derivative 3 is prepared by treating the pyridobenzimidazole derivative 2 with an appropriate alkylating agent such as ethoxymethyl chloride and a suitable base such as sodium hydride, $NaSi(TMS)_2$, or potassium carbonate/18-crown-6 in an appropriate solvent such as DMF at about 0° C. to room temperature for about 1–24 h or utilizing Mitsunobu conditions as described below. Base catalyzed hydrolysis and decarboxylation of the alkylated derivative 3 gives the enaminone derivative 4. Treatment of such enaminone derivative with a suitable electrophile such as a substituted aryl or alkyl isocyanate at room temperature for 2–24 h gives the corresponding pyridobenzimidazole derivative 1.

Scheme 2

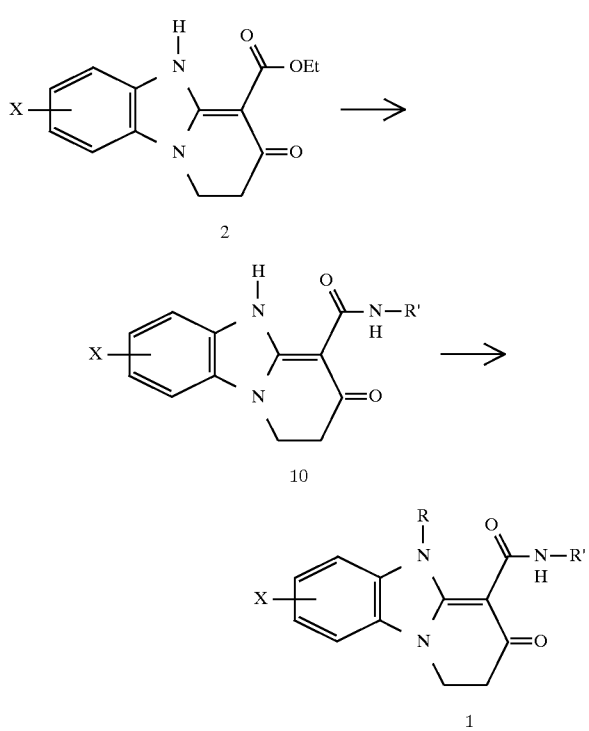

Alternatively, as shown in Scheme 2, the pyridobenzinidazole ester derivative 2 is heated to reflux with an appropriate substituted amine derivative (commercially available or prepared via methods known in the art; for example, see Turner, *J. Journal Of Organic Chemistry* 1983, 48, 3401–3408) in a suitable solvent such as xylene or dimethyl formamide for about 1–24 h to give the pyrido[1,2-a]benzimidazole amide derivative 10. Alkylated pyridobenzimidazole derivative 1 is then prepared by treating the pyridobenzimidazole derivative 10 with an appropriate alkylating agent such as ethoxymethyl chloride and a suitable base such as sodium hydride, $NaSi(TMS)_2$ or potassium carbonate/18-crown-6 in an appropriate solvent such as DMF at about 0° C. to room temperature for about 1–24 h. Other similarly used alkylating agents include 2-(dimethylamino)ethyl chloride and 2-(diisopropylamino) ethyl chloride. Alternatively the pyridobenzimidazole derivative 10 is selectively alkylated at the N5 position using the method of Mitsunobu (see Hughes, D. *Organic Reactions*, 42, 355–656) or the recently reported modified procedures (see Tsunoda *Tetrahedron Letters* 1993, 34 1639–1642 and Tsunoda *Chemistry Letters* 1994, 539–542). Treatment of pyridobenzimidazole derivative 10 with an appropriately substituted alcohol such as 2-(methoxy)ethanol and 1–5 equivalents of a suitable activating agent such as diethylazodicarboxylate (DEAD), azodicarbonyldipiperidine (ADDP) or 1,1-azobis(N,N-dimethylformamide) (TMAD) and an appropriate trisubstituted phosphine such as triphenyl phosphine or tributyl phosphine in an appropriate solvent such as benzene, THF, or methylene chloride at about 0° C. to room temperature for about 1–24 h provided the desired alkylated pyridobenzimidazole derivative 1.

Scheme 3

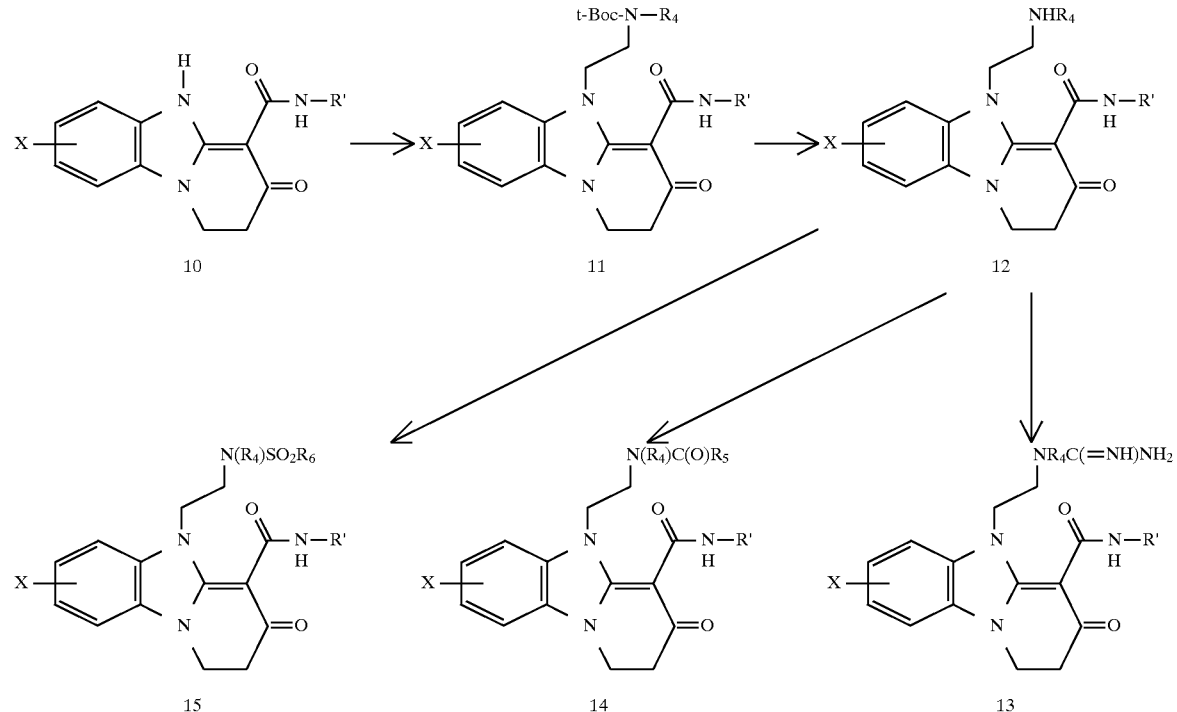

In a similar manner, the pyridobenzimidazole derivative 10 can be alkylated with an alchohol such as N-(t-butoxycarbonyl)ethanolamine under Mitsunobu conditions to give derivative 11 (Scheme 3). Removal of the Boc protecting group of 11 using acidic conditions such as 10% trifluoroacetic acid in a suitable solvent such as methylene chloride at room temperature for 1–24 h provides the aminoethyl derivative 12. The aminoethyl derivative 12 can be converted to an amidine or guanidinyl derivative. For example, treatment with 1-guanyl-3,5-dimethylpyrazole nitrate in a suitable solvent such as DMF at 0° C. to 100° C. for 1–24 h would give the guanidinoethyl derivative 13. Likewise, the aminoethyl derivative 12 can be treated with an appropriate substituted acylating agent such as acetyl chloride in a suitable solvent such as methylene chloride at 0° C. to 30° C. for 1–24 h to give the acylated derivative 14. Moreover, the aminoethyl derivative 12 can be treated with an appropriate substituted sulfonylating agent such as an alkyl sulfonyl chloride in a suitable solvent such as methylene chloride at 0° C. to 30° C. for 1–24 h to give the sulfonylated derivative 15.

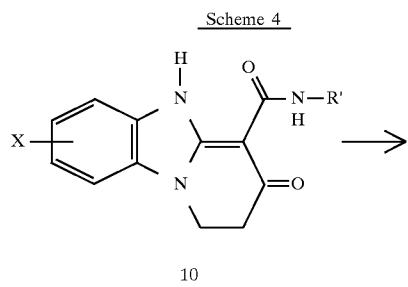

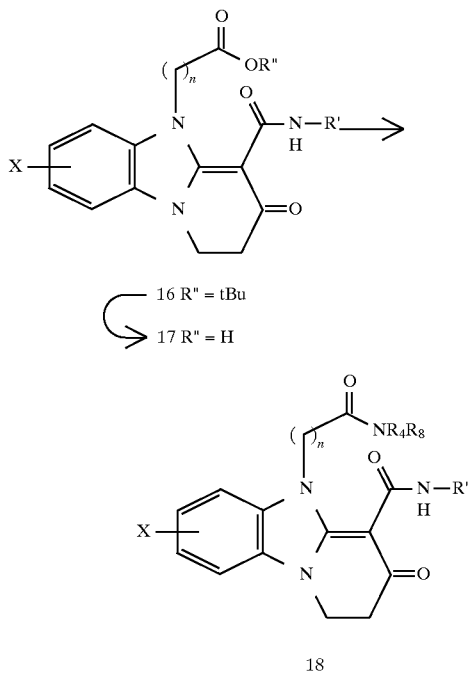

Alternatively, compounds of type 10 can be treated with a suitable electrophile such as tBu α-bromoacetate to give structures of type 16 (Scheme 4). Removal of the tBu group under mild acidic conditions leads to the free acid 17 which can then be converted to amides of type 18 by standard methods for amide formation such as DCC or CDI coupling reactions.

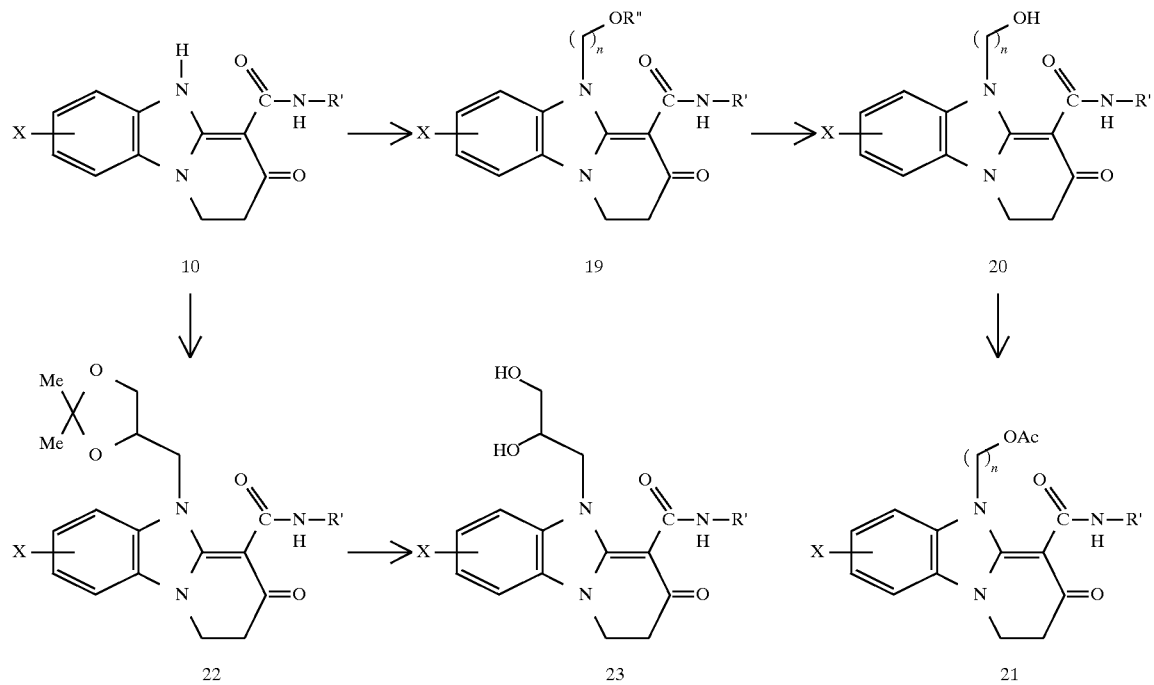

In a similar manner, ethers of type 19 can be prepared by use of the Mitsunobo reaction described earlier, such as with 2-(benzyloxy)ethanol or 2-(methoxy)ethanol (Scheme 5). The compounds of type 19 can then be converted to alcohols 20 under hydrogenolytic conditions such as the use of hydrogen gas in the presence of Pd/C in EtOH or MeOH or by the use of boron tribromide in a solvent such as methylene chloride. The free alcohols 19 can be derivatized in several different ways, such as conversion to acetates 21. Alternatively, conversion of 10 to the dioxolane 22 can be followed by cleavage of the acetonide to give diols of type 23.

Scheme 6

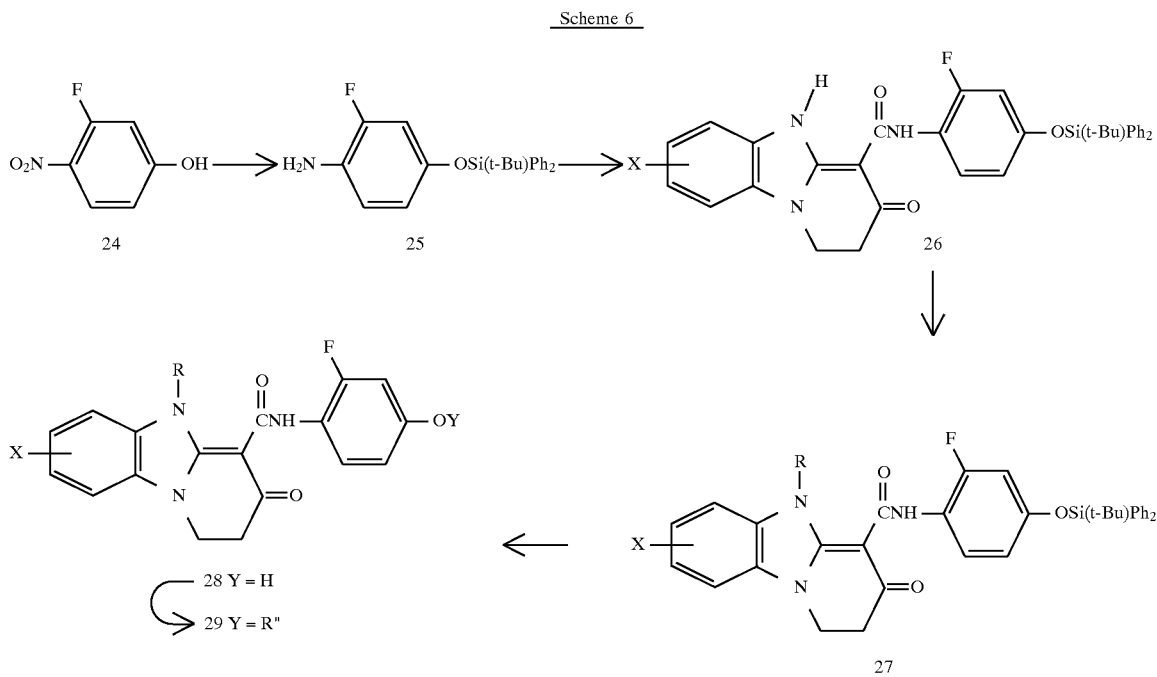

Certain compounds of the invention require the synthesis of particular anilines for condensation with compounds of type 2. For example, as shown in Scheme 6, phenol 24 is protected by silylation such as with reaction of BuPh$_2$SiCl, followed by reduction of the nitro group for example by the action of hydrogen gas and Pd/C in EtOH or MeOH to give 25, and then condensation with the appropriate ester to afford 26. Insertion of an alkyl radical onto N5 as before leads to 27, which produces 28 upon removal of the silyl group with fluoride such as by the use of CsF or nBu$_4$NF. The phenolic hydroxyl of 28 could be further derivatized to give compounds of type 29, such as by reaction of 28 with MeI or ClCH$_2$CH$_2$OMe.

Scheme 7

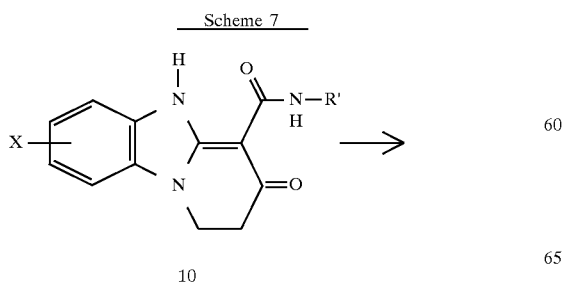

-continued
Scheme 7

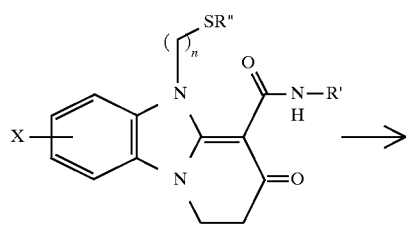

-continued
Scheme 7

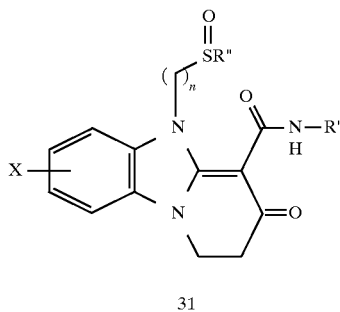

31

Additional compounds of type 1 could be prepared by treatment of 10 with a suitable electrophile containing a sulfur atom, such as $ClCH_2CH_nMe$ to give compounds such as those of type 30 (Scheme 7). Further conversion of 30 could be accomplished by additional reactions such as those involving oxidation to give derivatives of type 31.

The compounds of this invention were tested for affinity for the benzodiazepine sites of the GABA-A receptor. Since compounds which bind to this receptor can be useful in treating central nervous system disorders, the compounds were also tested in appropriate screens to evaluate specific activities. The results of the various screens are shown in Tables 1–3. Not all compounds were tested in each of the screens. A hyphen filling the space for a particular compound indicates that the compound was not tested in that screen.

Benzodiazepine Receptor Binding Assay

Selected compounds, which were prepared according to the experimental details given in the following examples, were tested for binding to the benzodiazepine site of the GABA-A receptor (Williams, M. et al., *J. Pharm. Exper. Therap.* 1988, 248, 89). The ability of the compounds of the invention to inhibit the binding of flunitrazepam to prepared receptors was assessed. For each sample, membranes from ca. 10 mg of tissue were incubated in a $K_2HPO_4$-buffered incubation medium (final concentration=2.0 mL). The concentration of ligand ($^3$H-flunitrazepam) was ca. 3 nM. Samples were incubated 10–20 min at 25° C., after which the membrane material and bound ligand was collected on glass fiber filter sheets using vacuum filtration. The collected material was washed with 10 mM HEPES buffered solution, and the radioactivity associated with each sample was measured by liquid scintillation spectrometry. The binding of the test drug to the receptor was determined by comparing the amount of radiolabeled ligand bound in control samples to the amount of ligand bound in the presence of the drug. Concentration-response data were analyzed in a variety of ways. The $IC_{50}$ was usually calculated by transforming the data to a log-logit format, then performing a linear regression analysis. This procedure provides a Hill coefficient as well as the $IC_{50}$ value. The $IC_{50}$ value, for all tested compounds is listed in Table 1. An $IC_{50}$ value of over 10,000 for a particular compound indicates that the compound was not active in this screen. This screen is a general one and compounds active here are considered active in treating one or more disorders of the central nervous system.

Assay to Determine the Suppression of Metrazol-Induced Convulsions in Adult Male Mice Selected compounds of the invention were tested for their ability to reduce metrazol-induced convulsions in mice (Swinyard, E. A. *J. Am. Pharm Assoc.* 1949, 38, 201). Male $CD_1$ mice, were fasted at least 16 hours, were divided into equal groups and test compounds or vehicle were administered parenterally. Water was not withheld except during the period of observations. At the time of suspected peak activity, anti-pentylenetetrazol (anti-metrazol) activity was evaluated by the subcutaneous administration of the $CD_{90}$ dose of metrazol (the dose of metrazol was determined from the dose-response curve producing clonic convulsions in 90% of animals that received the corresponding vehicle for this experiment). Metrazol was dissolved in 0.9% sodium chloride solution, and its dose volume was 10 ml/kg. Animals were housed individually for observation of clonic convulsions, tonic convulsions and death for a period of 30 min. Test compounds that blocked the clonic seizure component of the convulsion in at least 50% of the animals were considered active. The biological assay was considered to be valid if the effects of a known anticonvulsant (positive control) were detected, within the same experiment. Activity was reported as percent reduction of clonic convulsions from the vehicle group. The $ED_{50}$ values of active compounds were calculated by the method of probits (Finney, D. J. 1971. Probit Analysis. London: Cambridge University Press) and are listed in Table 1. An $ED_{50}$ value of greater than 30 indicates that an active dose for the compound being tested had not been determined. Compounds active in this screen are considered active anticonvulsant/antiepileptic agents.

Assay to Measure the Suppression of Anxiety in the Adult Male Rat

The anxiolytic activity of selected compounds of the invention was assessed by determining their ability to release (disinhibit) behavior that had been suppressed by punishment (Vogel, J. R. et al. *Psychopharmacology* 1971, 21, 1). Male rats were deprived of water for 48 hours and were deprived of food for 24 hours prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals.

The Wilcoxon rank-sum test (Mann-Whitney U-test) was used to test for an increase ($p<0.05$, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there is a significant difference in the median number of shocks tolerated between the drug-treated group and the control group. The minimum effective doses (MED) for the active compounds of the invention are listed in Tables 1 to 5. The MED was defined as the minimum dose of the drug-treatment as analyzed using the Wilcoxon rank-sum test (SAS; Statistical Analysis System, version 5.16). If the MED value is greater than 10, an active dose of the compound being tested had not yet been determined.

Assay To Measure The Suppression Of Trait Anxiety In Adult Male Rats ELEVATED PLUS-MAZE This is a behavioral model of trait anxiety, which is qualitatively unique in that it is based on the innate behavior of the animal and may model human anxiety traits. Trait anxiety may represent a type of anxiety with different underlying neurochemical mechanisms than state anxiety and may respond to a broader spectrum of anxiolytics.

Adult male Long-Evans hooded rats (Charles River Laboratories) were used. Animals had unlimited access to food and water except during the experiment but were deprived of food but not water for 18 hours before use. Test compounds were dissolved or suspended in 0.5% (w/v) aqueous methylcellulose solution containing 0.4% (v/v) Tween 80® and administered p.o. by gavage at a dose volume equivalent to 5 ml/kg. Doses of test compounds were calculated as active moiety. Each black plastic maze had two open arms and two arms with 40 cm high walls (enclosed arms), of equal length (50 cm), extending from the center at right angles, such that arms of similar type were opposite each other. Each plus-maze was elevated approximately 60 cm above the floor. Infrared photo-beams that crossed the entrance of each arm and the center of the maze detected the exploratory activity of an animal in the maze. At one hour after treatment, animals were placed on an open arm of the plus-maze facing the center. The 10-min test was initiated when the animal entered the center of the apparatus. Data collection was automated and was obtained while the investigator was outside of the laboratory.

The percent of total time spent (% time=100×[time in open arms divided by 600 sec]) and the percent of total entries made by animal in the open arms were calculated (% entries=100×[{entries into open arms, plus closed arms, plus the center} divided by the entries into the open arm]), and statistical significance was determined using the Wilcoxon rank sum test. Active treatments increased % time and/or % entries compared to vehicle-treated animals (p<0.05, one-tail).

Compounds are considered "active" if they display a <10,000 nM $IC_{50}$ in the $GABA_A$ receptor assay, a $\leq 30$ mg/kg $ED_{50}$ either ip or po in the mouse metrazol assay, or a $\leq 10$ mg/kg MED either ip or po in the rat conflict test.

Assay to Measure the Suppression of Conflict Anxiety In Squirrel Monkeys

Six adult male squirrel monkeys (Charles River Laboratories) were used in a procedure modified from that described by Gleeson and Barrett (1990). They were fed a diet of standard monkey chow and fruit to maintain their body weight at approximately 85% of their free-feeding weight and were fasted over-night before use. Test compounds were dissolved or suspended in 0.5% (w/v) aqueous methycellulose solution containing 0.4% (v/v) Tween 80® and administered p.o. by a pediatric oral feeding tube at a dose volume equivalent to 5 mL/kg. Doses of test compounds were calculated as active moiety. Tests were conducted with the monkey seated in a primate chair inside a light- and sound-attenuating ventilated cubicle (26" high× 28" wide×16" deep).

The session consisted of 10 three-min trials, separated by a one-min timeout. At the end of each three-min trial, a lever press (made between 3 and 3.5 min) produced the reward, a banana-flavored pellet. The superimposition of a punishment contingency involved the delivery of a brief (0.2 sec) electric shock (3 mA) to the tail for each $30^{th}$ response. Fear of punishment resulted in a greatly reduced rate of responding, and shocks were rarely if ever received. This suppressed responding constituted the behavioral baseline against which drug effects were measured.

Test compounds were evaluated once each week on the day after evaluating the effects of vehicle administration. Therefore, each animal was used as its own control. Variability in vehicle rates from week to week was minimized by using a forecast based on a time-series model using historical data with more weight being assigned to more recent vehicle experiments. Compounds were not tested in an individual animal if its vehicle response was outside the bounds of the lower or upper limit of the forecast. The effect of the test compound was calculated as the percent of the forecasted vehicle response rate (100×[response rate after treatment divided by the forecast of the response rate after vehicle administration]). Treatment effects were considered positive in an individual animal if its response rate exceeded the upper limit of its forecasted response rate (p<0.05). Active compounds produced a significant increase in response rate as a percent of the vehicle forecast (p<0.05, one tailed; one-sample t-test).

Tables 1–3 showing the biological activity of the compounds of the present invention appear at the end of the specification before the claims.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 1 to about 100 mg of the active ingredient, although other unit dosages may be employed.

In therapeutic use in treating disorders of the central nervous system in mammals, the compounds of this invention may be administered in an amount of from about 0.2 to 25 mg/kg per day. In therapeutic use as an anxiolytic, the compounds of the invention may be administered in an amount from about 0.2 to 25 mg/kg per day. In therapeutic use as an anticonvulsant/antiepileptic, the compounds of the invention may be administered in an amount from about 0.2 to 25 mg/kg per day. In therapeutic use as an agent for treating benzodiazepine overdoses, the compounds of the invention may be administered in an amount from about 0.2 to 25 mg/kg per day. In therapeutic use as a sedative/ hypnotic, a therapeutically effective amount is from about 0.2 to 25 mg/kg per day. As a muscle relaxant about 0.2 to 25 mg/kg per day of the compounds of this invention may be used. Determination of optimum dosages for a particular situation disease or condition may vary depending upon the situation, disease or condition of the patient being treated and is within the skill of the art.

EXAMPLES

The following examples describe the invention in greater detail and are intended to illustrate the invention, but not to limit it.

Melting point determinations were carried out on a Thomas Hoover or Mel-Temp melting point apparatus and are uncorrected. Each compound has two analytical results (elemental analysis, mp) that are listed in Table 4 and are consistent with its assigned structure. Nuclear magnetic resonance (NMR) spectra for hydrogen atoms were measured in the indicated solvent with tetramethylsilane (TMS) as the internal standard on a Bruker AM-360 (360 MHz), AM-400 (400 MHz), or AT-300 (300 MHz) spectrometer. The values are ewere measureparts per million downfield from TMS. The elemental analyses were measured by Robertson Microlit Labs (Madison, N.J.) and are expressed in percentage by weight of each element per total molecular weight. The mass spectra (MS) were determined on a Finnigan 3300 spectrometer (methane), using desorption chemical ionization techniques. Unless otherwise noted, the materials used in the examples were obtained from readily available commercial suppliers or synthesized by standard methods known to anyone skilled in the art of chemical synthesis. Substituent groups, which vary between examples, are hydrogen unless otherwise noted.

Example 1 (74)

7-Fluoro-1,2-dihydro-5-(2-dimethylaminoethyl)-3-oxo-N-(2-fluorophenyl)pyrido[1,2-a]benzimidazole-4-carboxamide hydrochloride hydrate (4:4:1)

To a suspended mixture of 2 (X=7-F; 3.31 g, 12.0 mmol) and 2-dimethylaminoethyl chloride hydrochloride (8.64 g, 60.0 mmol) in $CHCl_3$ (100 mL) was added benzyl triethylammonium chloride (300 mg) followed by 1N aqueous sodium hydroxide (100 mL). The resultant biphasic mixture was stirred at room temperature for 72 h. The reaction was transferred to a separatory funnel and the organic phase was drawn off into a flask and the aqueous layer was extracted with $CHCl_3$ (2×50 mL). The combined $CHCl_3$ solution was dried over $Na_2SO_4$, filtered and concentrated in vacuo to yield 3.54 g (85%) of 3 (X=7-F, R=2-dimethylaminoethyl) as a brownish solid. $^1$H NMR (300 MHz, $CDCl_3$) δ 7.18 (dd, J=2.28, 8.52 Hz, 1H), 7.13 (t, J=4.32, 4.41 Hz, 1H), 7.04 (ddd, J=2.22, 8.90, 8.95 Hz, 1H), 4.34 (q, J=7.08, 7.08, 7.08 Hz, 2H), 4.20 (t, J=6.88, 6.81 Hz, 2H), 4.12 (t, J=6.93, 6.94 Hz, 2H), 2.74 (t, 6.93, 6.94 Hz, 2H), 2.65 (t, J=6.90, 6.87 Hz, 2H), 2.23 (s, 6H), 1.42 (t, J=7.09, 7.09 Hz, 3H). MS (Cl—$CH_4$) MH$^+$=348. A solution of 3 (X=7-F, R=2-dimethylaminoethyl, 3.50 g, 10.0 mmol) in 3N aqueous NaOH and absolute ethanol (100 mL) was stirred at reflux for 6 h. The reaction mixture was concentrated, yielding an oil suspended in the aqueous layer. The suspended mixture was diluted with water (50 mL) and extracted with $CHCl_3$ (2×100 mL). The combined $CHCl_3$ solution was washed with brine (100 mL), dried over $Na_2SO_4$, filtered and concentrated in vacuo to provide 2.47 g (90%) of 4 [X=7-F, R=2-(dimethylamino)ethyl] as a brownish orange solid. Compound 4 was characterized by $^1$H NMR and carried on without further characterization. $^1$H NMR (300 MHz, $CDCl_3$) δ 6.95–6.81 (m, 3H), 4.95 (s, 1H), 4.06 (t, J=7.60, 7.60 Hz, 2H), 3.86 (t, J=7.22, 7.15 Hz, 2H), 2.73 (t, J=7.59, 7.60 Hz, 2H), 2.60 (t, 2H), 2.31 (s, J=7.21, 7.31 Hz, 3H). MS (Cl—$CH_4$) MH$^+$=276. A solution of 4 [X=7-F, R=2-(dimethylamino)ethyl; 1.25 g, 4.54 mmol] and 2-fluorophenyl isocyanate (620 μL, 5.53 mmol) in 1,2-dichloroethane (30 mL) was stirred at reflux for 9 h. 2-Fluorophenyl isocyanate (75 μL, 0.67 mmol) was added and the reaction was heated for an additional 2 h. The reaction mixture was concentrated in vacuo to provide a solid. The crude product was chromatographed on silica gel (elution with 5% MeOH in $CHCl_3$) to furnish 1.56 g (83%) of 74 as a light yellow solid. The free base was dissolved in MeOH (40 mL), filtered and acidified with conc. HCl in iPrOH until pH of 4.0. The acidified mixture was diluted with $Et_2O$ (100 mL) and the resulting precipitate was collected by filtration. Recrystallization from MeOH/$Et_2O$ gave 1.34 g of the HCl salt as a white crystalline solid. $^1$H NMR (300 MHz, DMSO-$d_6$) δ 12.35 (s, 1H), 10.70 (br s, 1H), 8.48 (ddd, J=1.30, 1.62, 8.44 Hz, 1H), 7.95 (dd, J=2.22, 9.15 Hz, 1H), 7.75 (dd, J=4.48, 8.89 Hz, 1H), 7.34 (ddd, J=2.28, 7.24, 9.54 Hz, 1H), 7.24 (ddd, J=0.97, 4.68, 8.77 Hz, 1H), 7.14 (t, J=7.40, 7.00 Hz, 1H), 7.01 (dddd, J=1.62, 8.44, 7.50, 7.50 Hz, 1H), 4.69 (t, J=7.47, 7.48 Hz, 2H), 4.34 (t, J=6.68, 6.68 Hz, 2H), 3.67 (m, 2H), 2.84 (s, 3H), 2.72 (t, J=6.69, 6.69 Hz, 2H). MS (Cl—$CH_4$) MH$^+$=413.

In a similar manner, using the appropriate isocyanates, the following compounds were also prepared via the method shown in Scheme 1: 49, 73, 101, 105, 120–122, 124–126, 129, 130, 132–136, 139–140, and 143–147.

Example 2 (63)

7-Fluoro-1,2-dihydro-5-[N,N-di(benzyl)-2-aminoethyl]-3-oxo-N-(2,6-difluorophenyl)pyrido[1,2-a]benzimidazole-4-carboxamide A bipasic mixture of crude 10 (X=7-F, Ar=2-FPh; 3.59 g, 10.00 mmol), benzyltriethylammonium chloride (1.14 g, 5.00 mmol), N-(2-chloroethyl)-dibenzylamine hydrochloride (11.0 g, 37.1 mmol), 1N NaOH (70 mL), and chloroform (150 mL) was stirred stirred vigorously for 1 d. The aqueous layer was separated and extracted with chloroform (100 mL). The organic layer was dried over $Na_2SO_4$, filtered, concentrated in vacuo and the isolated crude product was chromatographed on silica gel (5:95 methanol/chloroform). This free base was dissolved in methanol (50 ml), acidified with concentrated HCl in methanol solution to a pH of 3.5. Recrystallization of the HCl salt twice from methanol/ether provided 0.67 g of 63 (10%) as a white powder. MS(Cl—$CH_4$) MH$^+$=583. H-1 NMR (300 MHz, $CDCl_3$) δ 2.80 (t, 2H), 4.2 (t, 2H), 4.3–4.4 (m, 4H), 4.9 (t, 2H), 6.9–7.05 (m, 3H), 7.15–7.20 (m, 3H), 7.4 (m, 5H), 7.75 (m, 5H), 11.4 (s, 1H), 13.0 (br s, 1H).

In a similar manner where prepared compounds 34, 43, 45, 54–56, 64, and 68–72, and 88.

Example 3 (62)

7-Fluoro-1,2-dihydro-5-[N-(4-fluorobenzyl)-2-aminoethyl]-3-oxo-N-(2-fluorophenyl)pyrido[1,2-a]benzimidazole-4-carboxamide A bipasic mixture of crude 10 (X=7-F, Ar=2-FPh, 3.41 g, 10.00 mmol), benzyltriethylammonium chloride (1.14 g, 5.00 mmol), 4-fluorobenzyl chloride (6.0 mL, 50.0 mmol), 2-(methylamino)ethylchloride hydrochloride (6.45 g, 50.0 mmol), 1N NaOH (70 mL), and chloroform (150 mL) was stirred vigorously for 3 d, and then additional quanities of 5 ml (41.7 mmol) of 4-fluorobenzyl chloride, 2 g (15.5 mmol) of 2-methylaminoethyl chloride hydrochloride, and 0.6 g (2.63 mmol) benzyltriethylammonium chloride, and 20 mL of 1N NaOH were added to the reaction mixture. The aqueous layer was separated and extracted with chloroform (150 mL), and the organic layer was dried over $Na_2SO_4$, filtered, concentrated in vacuo. The resultant product was chromatographed on silica gel (5:5 to 6:4 ethyl acetate/hexane) to give 4.78 g of impure product. A 1 g quantity of this free base was dissolved in methanol (50 ml), acidified with concentrated HCl in methanol to a pH of 3.0. Recrystallization of the HCl salt twice from methanol/ether provided 0.24 g of a white powder of 62. MS(Cl—$NH_3$) $MH^+$=507 (100%). H-1 NMR (300 MHz, $CDCl_3$) δ 2.70–2.80 (m, 5H), 3.75 (m, 2H), 4.30–4.40 (m, 3H), 4.45–4.55 (m, 1H), 4.7 (t, 2H), 6.9–7.0 (m, 1H), 7.02–7.12 (m, 1H), 7.20–7.30 (m, 3H), 7.35 (t, 1H), 7.6–7.8 (m, 3H), 7.9 (m, 1H), 8.4 (t, 1H), 11.25 (br s, 1H), 12.3 (s, 1H).

In a similar manner was prepared compound 65.

Example 4 (160)

7-Fluoro-1,2-dihydro-5-[2-(methoxy)ethoxymethyl]-3-oxo-N-(2-fluorophenyl)pyrido[1,2-a]benzimidazole-4-carboxamide To a 50 mL three necked round bottom flask was added NaH (258 mg, 6.45 mmol, 60% in oil, washed 2×20 mL pentane), anhydrous DMF (20 mL) and 10 (X=7-F, Ar=2-FPh; 1.70 g, 5.00 mmol). Upon complete evolution of $H_2$ gas, the reaction solution was treated with 15-crown-5 (1.00 mL, 5.03 mmol) followed by 2-(methoxy)ethoxymethyl chloride (800 μL, 7.00 mmol). The resultant reaction mixture was stirred at room temperature for 42 h, poured into brine and extracted into $CHCl_3$ (2×100 mL). The $CHCl_3$ solution was washed with $H_2O$ (6×100 mL), dried over $Na_2SO_4$ and concentrated. The resulting amber oil was purified by chromatography (silica gel, 3:7 hexane/ethyl acetate) to provide 1.97 g of crude 1 60. Recrystallization from ethyl acetate/hexane gave 1.39 g of 160. MS (auto Cl—$NH_3$) $MH^+$=430. $^1$H NMR (300 MHz, DMSO-$d_6$) δ 12.05 (s, 1H), 8.42–8.36 (m, 1H), 7.38 (dd, J=2.27, 8.47 Hz, 2H), 7.20 (dd, J=4.26, 8.80 Hz, 1H), 7.13–7.06 (m, 3H), 7.01–6.94 (m, 1H), 5.83 (s, 2H), 4.15 (t, J=6.88, 6.88 Hz, 2H), 3.50–3.48 (m, 2H), 3.41–3.39 (m, 2H), 3.22 (s, 3H), 2.85 (t, J=6.88, 6.88 Hz).

In a similar manner was prepared compounds 77, 78, 82, 85, 89, 90, 98, 103–104, 111–113, 115, 116, 123, 127, 128, 158–159, 167, 172, 173, and 182.

Example 5 (59)

7-Fluoro-1,2-dihydro-5-[2-(methylamino)ethyl]-3-oxo-N-(2-fluorophenyl)pyrido[1,2-a]benzimidazole-4-carboxamide hydrochloride hydrate (4:4:5)

To a suspended solution of 10 (X=7-F, Ar=2-FPh, 5.12 g, 15.0 mmol) in $CH_2Cl_2$ (250 mL) under $N_2$ atmosphere was added triphenylphosphine (7.87 g, 30.0 mmol) followed by N-benzyl-2-(methylamino)ethanol (4.90 mL, 30.2 mmol). This heterogenous mixture was cooled to 0° C. and treated with diethylazodicarboxylate (DEAD, 4.80 mL, 30.5 mmol) dropwise over a 25 min period. Following addition, the ice bath was removed and the reaction mixture was stirred at room temperature for 18 h. The reaction mixture was concentrated in vacuo to give an oil, which was purified by flash chromatography (silica gel, eluting with 20% hexane/ethyl acetate) to afford 12 g of 1 [X=7-F, Ar=2-FPh, R=Bz(Me)$NCH_2CH_2$] as a light yellow solid. MS (Cl—$CH_4$) $MH^+$=489. A mixture of 1 [X=7-F, Ar=2-FPh, R=Bz(Me)$NCH_2CH_2$, 12.0 g), 10% palladium on carbon (7.32 g) and ammonium formate (4.72 g, 75.0 mmol) in absolute methanol (125 mL) was stirred at reflux under $N_2$ atmosphere for 2 h. The reaction mixture was filtered through Celite and then concentrated in vacuo to provide 9.69 g of 59 as a tacky solid. Purification by chromatography (silica gel, eluting with 7% MeOH/$CHCl_3$) afforded 3.56 g (60% yield) of 59 as a white solid, which was converted to its HCl salt. H-1NMR (300 MHz, DMSO-$d_6$) δ 8 12.45 (s, 1H), 8.88 (br s, 1H), 8.48 (ddd, J=1.30, 1.62, 8.44 Hz, 1H), 7.87 (dd, J=2.25. 9.16 Hz, 1H), 7.75 (dd, J=4.46, 8.87 Hz, 1H), 7.34 (ddd, J=2.28, 7.24, 9.54 Hz, 1H), 7.24 (ddd, J=0.97, 4.68, 8.77 Hz, 1H), 7.14 (t, J=7.40, 7.00 Hz, 1H), 7.01 (dddd, J=1.62, 8.44, 7.50, 7.50 Hz, 1H), 4.71 (t, J=6.50, 6.50 Hz, 2H), 4.34 (t, J=6.64, 6.64 Hz, 2H), 3.41 (m, 2H), 2.72 (t, J=6.66, 6.66 Hz, 2H), 2.57 (s, 3H). MS (AutoCl—$NH_3$) $MH^+$=399.

In a similar manner as for the preparation of 1 [X=7-F, R'=2-FPh, R=Bz(Me)$NCH_2CH_2$] described above was obtained compounds 41, 66, 67, 80, 83, 84, 86, 87, 91, 102, 106–110, 117, 118, 131, 137, 138, 141, 142, 148–157, 161, 163, 165, 166, 175, 176, 179, and 181. In a similar manner as for the preparation of 59 was prepared compound 52.

Example 6 (48)

7-Fluoro-1,2-dihydro-5-[2-(trifluoromethylsulfonamido)ethyl]-3-oxo-N-(2-fluorophenyl)pyrido[1,2-a]benzimidazole-4-carboxamide In a similar manner as that described in Example 3 using DEAD, compound 58 (X=7-F, Ar=2-FPh) was prepared from 10 (X=7-F, Ar=2-FPh, 49.0 g, 143.0 mmol) and N-(t-butoxycarbonyl)ethanolamine (75.5 mL, 490.0 mmol) in 62% yield (43.0 g). To a solution of 58 in methylene chloride (50 mL) was added trifluoroacetic acid (100 mL). The resulting yellow solution was stirred an additional 30 min, cooled to 0° C. and then treated dropwise with 3N sodium hydroxide until basic. The resultant white solid was collected by filtration and dried to give 11.1 g (99%) of 57. To a solution of 57 (1.0 g, 2.6 mmol) in THF (20 mL) was added trifluoromethanesulfonyl chloride (0.028 mL, 2.6 mmol) followed by dropwise addition of triethylamine (0.4 mL, 2.6 mmol). The resulting white suspension was stirred at room temperature for 15 min. The reaction mixture was concentrated in vacuo and the resulting amber oil was purified by chromatography (silica gel, methylene chloride). The resultant white solid which was recrystallized from isopropanol to obtain 48 (0.25 g, 18.6%) as a white crystalline solid: mp>200° C.; H-1 NMR ($Me_2SO$-$d_6$) δ 12.30 (s, 1H), 9.55 (bs, 1H), 8.45–8.52 (t, 1H), 7.69–7.80 (m, 2H), 7.20–7.35 (m, 2H), 7.10–7.20 (t, 1H), 6.95–7.04 (m, 1H), 4.69–4.80 (m, 2H), 4.30–4.40 (t, 2H), 3.47–3.59 (m, 2H), 2.63–2.72 (t, 2H). FAB MS $MH^+$=517.

In a similar manner was prepared compounds 35, 37, 39, 42, 44, 46, 47, 50, 51, 53, 75, 76, 79, and 81 (cleavage of the t-butoxycarbonyl group from 80), using the appropriate reagents.

Example 7 (40)

7-Fluoro-1,2-dihydro-5-[2-(dimethylamidino)ethyl]-3-oxo-N-(2-fluorophenyl)-pyrido[1,2-a]benzimidazole-4-carboxamide To a solution of 57 in ethanol (10 mL) was added (chloromethylene)dimethylammonium chloride (0.140 g, 1.1 mmol) and stirred for 1 h at room temperature. Triethylamine (0.130 g, 0.0013 mol) was added causing the reaction to clear partially. After stirring for an additional hour, $CH_2Cl_2$ (100 mL) was added followed by 3N NaOH solution (30 mL) with thorough mixing. The organic layer was separated and then concentrated in vacuo to give a clear oil which slowly crystallized. This material (0.440 g) was dissolved in ethanol (5 mL) and treated with fumaric acid (0.116 g) with heating. On cooling and after the addition of a small amount of $Et_2O$, a white crystalline solid was obtained which was recrystallized from $EtOH/Et_2O$ to give 40 (0.288 g, 56%) as a white crystalline solid: mp200°–202° C.; H-1 NMR ($Me_2SO-d_6$) δ 8.55–8.45 (m, 1H), 7.90–7.80 (m, 1H), 7.77–7.70 (m, 1H), 7.65 (s, 1H), 7.35–9.90 (m, 4H), 4.80–4.72 (m, 2H), 4.38–4.22 (m, 2H), 3.60–3.50 (m, 2H), 2.78 (s, 6H), 2.75–2.60 (m, 2H). MS=440 ($MH^+$).

Compound 33 was prepared in a similar manner using the appropriate guanidine-forming reagent.

Example 8 (184)

7-Fluoro-1,2-dihydro-5-[2-(methylthio)ethyl]-3-oxo-N-(2-fluorophenyl)pyrido[1,2-a]benzimidazole-4-carboxamide Diethyl azidodicarboxyiate (1.2 mL, 8.79 mmol) was added to a suspension of 10 (X=7-F, Ar=2-FPh, 1.0 g, 2.93 mmol), triphenylphosphine (2.31 g, 8.79 mmol) and 2-(methylthio)ethanol (0.77 mL, 8.79 mmol) in THF (20 mL) at 0° C.

The resultant red solution was stirred at 0° C. for 1 h, and the solvent was evaporated in vacuo. The residue was purified by flash chromatography, using 2% $CH_3OH$ in $CH_2Cl_2$ as the eluant. Recrystallization from isopropanol gave 184, 0.91 g (75%), as a colorless solid: mp 195°–196°C. H-1 NMR ($CDCl_3$) δ 2.07 (s, 3H), 2.86 (t, 2H), 2.94 (t, 2H), 4.19 (t, 2H), 4.69 (t, 2H), 6.94–7.04 (m, 1H), 7.07–7.18 (m, 4H), 7.25 (dd, 1H), 8.44 (dd, 1H), 12.05 (br s, 1H). MS m/e 416 ($MH^+$).

Example 8 (185)

7-Fluoro-1,2-dihydro-5-[2-(methylsulfoxy)ethyl]-3-oxo-N-(2-fluorophenyl)pyrido[1,2-a]benzimidazole-4-carboxamide Sodium periodate (1.17 g, 5.49 mmol) was added to a solution of 184 (0.57 g, 1.37 mmol) in 10 mL of ethanol, 5 mL of chloroform, and 2 mL of water and stirred for 1 h. The resultant mixture was poured into $CH_2Cl_2$ (100 mL) and water (100 mL) and the organic layer was separated. The solvent was evaporated in vacuo, and the residue purified by flash chromatography, using 2% $CH_3OH$ in $CH_2Cl_2$ as the eluant to give a colorless solid of 185, (0.227 g, 37%) mp 218°–220° C. H-1 NMR ($CDCl_3$): δ 2.67 (s, 3H), 2.78–2.96 (m, 2H) 3.23–3.36 (m, 1H), 3.47–3.61 (m, 1H), 4.10–4.27 (m, 2H), 4.75–4.98 (m, 2H), 6.96–7.04 (m, 1H), 7.09–7.18 (m, 3H), 7.22–7.30 (m, 1H), 7.46 (dd, 1H), 8.35 (dd, 1H), 12.05 (br s, 1H); MS m/e 432 ($MH^+$).

Example 10 (99)

7-Fluoro-1,2-dihydro-5-ethoxymethyl-3-oxo-N-(2-fluoro-4-hydroxyphenyl)pyrido[1,2-a]benzimidazole-4-carboxamide To a solution of 3-fluoro-4-nitrophenol 24 (6.29 g, 40.0 mmol) and imidazole (3.27 g, 48.0 mmol) in anhydrous dimethylformamide (40 mL) was added t-butyl diphenyl chlorosilane (12.0 mL, 46.1 mmol) at room temperature. The resulting mixture was stirred at room temperature under $N_2$ atmosphere for 4 h. The reaction mixture was then diluted with aqueous sodium chloride (100 mL) and extracted with $CHCl_3$ (2×125 mL). The $CHCl_3$ solution was washed with water (5×200 mL), dried over $Na_2SO_4$, filtered and concentered to provide the silyl ether as a brown solid (17.81 g). The material and 10% Pd/C (1.02 g) in EtOAc (120 mL) was placed in a Parr bottle and pressurized at 40 psig with hydrogen. After 18 hr, the resulting mixture was filtered through Celite and concentrated in vacuo to give desired aniline 25 as a brown oil (17.22 g, quantitative yield). A heterogenous mixture of 2 (X=7-F, 8.82 g, 32.0 mmol) and 25 (17.11 g, ca 36.0 mmol) in xylenes (400 mL) was heated at reflux for 4 h. Upon removal of the solvent (200 mL) from the reaction mixture by distillation and subsequent cooling of the reaction mixture to room temperature, a moist brown solid was collected by filtration. This solid was washed with $Et_2O$ and dried under vacuum to afford desired amide 26 (X=7-F) as a brown solid (17.20 g). To a cooled (20° C. water bath) mixture of 26 thus formed (12.07 g, ca 20.0 mmol) in DMF (60 mL) was added chloromethyl ethyl ether (4.50 mL, 48.5 mmol) and diisopropylethylamine (9.1 mL, 52.2 mmol). The resultant mixture was stirred at room temperature for 4 h and diluted with $H_2O$. A solid residue plated out along sides of the reaction flask and the aqueous layer was decanted. The residue was dissolved in $CHCl_3$, dried over $Na_2SO_4$ and concentrated in vacuo to furnish N-ethoxymethyl product 27 (X=7-F, R=$EtOCH_2$) as a brown solid. This solid was chromatographed on silica gel (elution with 2% MeOH in $CHCl_3$) to provide 10.95 g (83%) of flaky brown solid. To a solution of this solid (5.28 g, ca 8.01 mmol) in anhydrous THF (100 mL) was added tetrabutylammonium fluoride (1M in THF; 9.3 mL, 9.3 mmol) at room temperature for 2 h. The reaction was acidified with 15 ml of 1N aqueous HCl, further diluted with $H_2O$ (100 mL), and extracted with 85:15 $CH_2Cl_2$/THF. The organic solution was dried, filtered and concentrated in vacuo to afford 99 as a brown solid. This crude product was chromatographed on silica gel (elution with 15% THF in $CH_2Cl_2$) to yield 3.35 g of an off-white solid. Crystallization from acetone/hexane and subsequent drying in a vacuum oven at 60° C. for 1 d yielded 2.73 g (82%) of 99, mp 203°–205√ C. H-1 NMR (300 MHz, acetone-$d_6$) δ 12.05 (s, 1H), 8.40 (s, 1H, OH), 8.30 (t, J=9.0 Hz, 1H), 7.59 (dd, J=4.39, 8.83 Hz, 1H) 7.52 (dd, J=2.33, 8.69 Hz, 1H), 7.19 (ddd, J=2.31, 9.25, 9.34 Hz), 6.67–6.58 (m, 2H), 5.84 (s, 2H), 4.34 (t, J=6.88, 6.88 Hz, 2H), 3.32 (q, J=7.08, 7.00, 6.99 Hz, 2H), 2.78 (t, J=6.97, 6.79 Hz, 2H), 1.00 (t, J=7.00, 6.99 Hz, 3H). MS(Cl—$NH_3$) $MH^+$=416.

Example 11 (97)

7-Fluoro-1,2-dihydro-5-ethoxymethyl-3-oxo-N-(2-fluoro-4-methoxyphenyl)pyrido[1,2-a]benzimidazole-4-carboxamide To a heterogeneous mixture of 99 (0.50 g, 1.20 mmol), potassium carbonate (249 mg, 1.80 mmol), 18-crown-6 (318.3 mg, 1.20 mmol), and iodomethane (225 μL, 3.61 mmol) in anhydrous DMF (10 mL) was stirred at room temperature for 2.5 d. The reaction mixture was diluted with aqueous NaCl solution (100 mL) and extracted into $CHCl_3$ (2×75 mL). The $CHCl_3$ solution was washed with $H_2O$ (4×100 mL), dried over $Na_2SO_4$, filtered, and concentrated in vacuo to provide a crude product. The crude product was chromatographed on silica gel (1:4 hexane/ethyl acetate) and subsequently recrystallized from ethyl acetate/hexane to give 0.35 g (68%) of 97 as white crystals. MS(Cl—NH$_3$) MH$^+$=400 (100%). H-1 NMR (300 MHz, CDCl$_3$) δ 1.1 (t, 3H), 2.85 (t, 2H), 3.30 (q, 2H), 3.70 (s, 3H), 4.15 (t, 2H), 4.55 (t, 2H), 4.8 (t, 2H), 5.75 (s, 2H), 6.66–6.74 (m, 2H), 7.06–7.12 (m, 1H), 7.18–7.22 (m, 1H), 7.35 (m, 1H), 8.15 (t, 1H), 11.7 (s, 1H).

In a similar manner using the appropriate electrophiles was prepared compounds 75, 76, 78, 83, and 174.

Example 12 (61)

7-Fluoro-1,2-dihydro-5-[N-(2-fluorophenyl)-2-acetamido]-3-oxo-N-(2-fluorophenyl)pyrido[1,2-a]benzimidazole-4-carboxamide To a 100 mL round bottom flask was added a solution of the sodium salt of 10 (X=7-F, 1.42 g, 4.00 mmol), prepared separately by reaction of 10 (X=7-F) with NaOEt/EtOH (1.1 mol-equiv.) followed by evaporation of the solvent, and 15-crown-5 (0.80 mL, 4.00 mmol) in acetonitrile (40 mL). The resultant mixture was treated with N-[(2-fluoro)phenyl]-2-bromoacetamide (928 mg, 4.00 mmol) and allowed to stir at room temperature for 16 h. The reaction mixture was concentrated in vacuo and the isolated crude product was chromatographed on silica gel (gradient elution with 5:5–7:3 ethyl acetate/hexane) to provide 980 mgs, recrystallization of which from acetone/ether gave 480 mgs (25%) of a flaky white solid (61). MS(Cl—NH$_3$) MH$^+$=493 (100%). H-1 NMR (300 MHz, DMSO-d$_6$) δ 2.60 (t, 2H), 4.4 (t, 2H), 5.3 (s, 2H), 6.9–7.2 (m, 7H), 7.65–7.75 (m, 2H), 7.9 (t, 1H), 8.4 (t, 1H), 10.1 (s, 1H), 12.2 (s, 1H).

Compound 60 was prepared in a similar manner.

Example 13 (36)

7-Fluoro-1,2-dihydro-5-[N-(2-cyanoethyl)-2-acetamido]-3-oxo-N-(2-fluorophenyl)pyrido[1,2-a]benzimidazole-4-carboxamide To a 100 mL round bottom flask was weighed 60% NaH dispersed in mineral oil (335 mg, 8.37 mmol). Under N$_2$ atmosphere the NaH was rinsed with pentane (2×20 mL), suspended in anhydrous DMF (40 mL), and treated with 10 (X=7-F, Ar=2-FPh, 2.39 g, 7.00 mmol). Then 15-crown-5 (1.40 mL, 7.05 mmol) and t-butyl bromoacetate (1.55 mL, 10.5 mmol) were added sequentially to the reaction mixture. The resultant mixture was stirred at room temperature for 2.5 d, then 116 mg (2.90 mmol) of 60% NaH and 200 μL (1.40 mmol) of t-butyl bromoacetate were added and the reaction stirred for an additional 1 d. The reaction mixture was then diluted with aqueous NaCl solution (150 mL) and extracted with CHCl$_3$ (200 mL). The CHCl$_3$ solution was washed with H$_2$O (4×200 mL), dried over Na$_2$SO$_4$, filtered, concentrated in vacuo and washed with Et$_2$O to give 2.68 g of a beige solid of 177. MS (Cl—NH$_3$) MH$^+$=456. A solution of 2.04 g (4.57 mmol) of this material in methylene chloride (60 mL) was treated with trifluoroacetic acid (20 mL, 260 mol) and stirred at room temperature for 2.5 d. The reaction solution was filtered and diluted with Et$_2$O (450 mL). The mixture was placed in the refrigerator for 18 h and 1.60 g (87%) of a beige solid of 178 was isolated upon filtration and drying at 70° C. in a vacuum oven. MS(Cl—NH$_3$) MH$^+$=400. Triethylamine (2.80 mL, 20.0 mmol) was added to a cooled (0° C.) solution of 178 (1.60 g, 4.00 mmol), diethylcyanophosphonate (940 μL, 6.20 mmol), and 3-aminopropionitrile (315 μL, 4.28 mmol) in anhydrous DMF (15 mL). The reaction mixture was stirred for 1 h, diluted with aqueous NaCl, and extracted with CHCl$_3$. Product precipitated out of the organic and aqueous phases. The organic solution was drawn off and concentrated. Both phases were filtered and washed with Et$_2$O to provide a solid (1.96 g) of 36. Recrystallization of crude product from CHCl$_3$/MeOH gave 1.31 g (72%) of a beige amorphous solid (36). MS (Cl—NH$_3$) MH$^+$=452 (100%). H-1 NMR (300 MHz, DMSO-d$_6$) δ 2.6 (t, 2H), 2.7 (t, 2H), 3.30–3.40 (m, 3H), 4.35 (t, 2H), 4.9 (s, 2H), 6.90–7.00 (m, 1H), 7.1–7.3 (m, 3H), 7.5–7.6 (m, 1H), 7.65–7.75 (m, 1H), 8.4–8.6 (m, 2H), 12.2 (s, 1H).

Compound 32 was prepared in a similar manner using histamine as the amine component.

Example 14 (171)

7-Fluoro-1,2-dihydro-5-[2-(benzyloxy)ethyl]-3-oxo-N-(2-fluorophenyl)pyrido[1,2-a]benzimidazole-4-carboxamide To a cooled (0° C.), suspended mixture of 10 (X=7-F, R'=2-FPh, 2.38 g, 6.98 mmol), triphenylphosphine (2.75 g, 10.5 mmol) and 2-benzyloxyethanol (1.50 mL, 10.5 mmol) in CH$_2$Cl$_2$ (140 mL) was added DEAD (1.65 mL, 10.5 mmol) dropwise over a 20 min period. The reaction mixture was stirred at 0° C. for 20 min and at room temperature for 2 h. Additional triphenylphosphine (0.92 g, 3.5 mmol), 2-benzyloxyethanol (0.50 mL, 3.5 mmol) and DEAD (0.55 mL, 3.5 mmol) were added and the reaction stirred for 4 h. The reaction mixture was concentrated in vacuo and the isolated crude product was chromatographed on silica gel (elution with 7:3 ethyl acetate/hexane) to provide 0.88 g of product, recrystallization of which from acetone/ether gave 580 mg (25%) of a white amorphous solid of 171. MS(Cl—NH$_3$) MH$^+$=476 (100%). H-1 NMR (300 MHz, CDCl$_3$) δ 2.75 (t, 2H), 3.9 (t, 2H), 4.25 (t, 2H), 4.4 (s, 2H). 4.7 (t, 2H), 6.9–7.0 (m, 1H), 7.02–7.12 (m, 5H), 7.15–7.20 (m, 1H), 7.4 (dd, 1H), 8.4 (t, 1H), 12.0 (s, 1H).

In a similar manner was prepared compound 170.

Example 15 (168)

7-Fluoro-1,2-dihydro-5-(2-hydroxyethyl)-3-oxo-N-(2-fluorophenyl)pyrido[1,2-a]benzimidazole-4-carboxamide A heterogenous mixture of 171 (3.80 g, ca 5.00 mmol), 10% palladium on carbon (0.70 g), and concentrated HCl (0.4 mL) in MeOH (100 mL) was shaken on Parr apparatus under 55 psig of hydrogen at room temperature for 4 h. The mixture was filtered through Celite. The filtrate was neutralized with 2.0 mL of Et$_3$N and concentrated in vacuo to provide a greenish solid. The solid was triturated with EtOAc and recrystallized from a 3:2 mixture of EtOAc/MeOH to afford 0.52 g (27%) of 168 as white crystals. MS(Cl—NH$_3$) MH$^+$=386 (10%). H-1 NMR (300 MHz, DMSO-d$_6$) δ 2.70 (t, 2H), 3.7 (dt, 2H), 4.35 (t, 2H), 4.6 (t, 2H), 4.8 (t, 1H, exchangeableH), 6.9–7.0 (m, 1H), 7.1 (t, 1H), 7.2–7.3 (2H), 7.7–7.8 (m, 2H), 8.5 (t, 1H).

In a similar manner was prepared compound 169, and using the same debenzylation procedure described above, compound 52 was prepared from 56.

Example 16 (119)

7-Fluoro-1,2-dihydro-5-(2-acetoxyethyl)-3-oxo-N-(2-fluorophenyl)pyrido[1,2-a]benzimidazole-4-carboxamide A heterogeneous mixture of 168 (0.50 g, 1.30 mmol), acetic anhydride (10.0 mL, 105 mmol) and pyridine (7.0 mL, 86.5 mmol) in CHCl₃ was stirred at room temperature. Within one hour of stirring, the reaction mixture became homogeneous. The reaction mixture was stirred for 5 h, diluted to 150 mL with CHCl₃, washed with H₂O (5×100 mL) and dried over Na₂SO₄. The CHCl₃ solution was filtered and concentrated in vacuo to provide 0.50 g of a solid product. Purification of the crude product was achieved by column chromatography on silica gel (elution with 1:4 hexane/ethyl acetate), and subsequent recrystallization from ethyl acetate/hexane provided 0.38 g (68%) of 119 as a white amorphous solid. MS(Cl—NH₃) MH⁺=428 (100%). H-1 NMR (300 MHz, CDCl₃) δ 1.90 (s, 3H), 2.75 (t, 2H), 4.15 (t, 2H), 4.50 (t, 2H), 4.8 (t, 2H), 6.9–7.0 (m, 1H), 7.02–7.12 (m, 5H), 7.15–7.20 (m, 1H), 7.2–7.3 (m, 1H), 8.4 (t, 1H), 12.0 (s, 1H).

In a similar manner, using the appropriate electrophile, was prepared compound 180.

Example 17 (114)

7-Fluoro-1,2-dihydro-5-[2-(methoxycarbonyloxy) ethyl]-3-oxo-N-(2-fluorophenyl)pyrido[1,2-a] benzimidazole-4-carboxamide To a heterogeneous mixture of 168 (0.50 g, 1.30 mmol) and methyl chloroformate (2.0 mL, 26 mmol) in CHCl₃ (50 mL) was added pyridine (1.0 mL, 12.3 mmol) at 0° C. The reaction mixture was stirred at room temperature for 8 h. Then the reaction mixture was treated with 0.5 mL of the chloroformate reagent and 0.5 mL of pyridine and stirred overnight. The reaction mixture was diluted with CHCl₃ (50 mL), washed with aqueous NaHCO₃ (3×50 mL), and H₂O (2×50 mL). The CHCl₃ solution was concentrated in vacuo to provide 0.62 g of crude product. Purification of this material was achieved by column chromatography on silica gel (1:4 ethyl acetate/hexane) and recrystallization from ethyl acetate/hexane to provide 0.36 g (62%) of 114 as a white amorphous solid. MS(Cl—NH₃) MH⁺=444 (100%). H-1 NMR (300 MHz, CDCl₃) δ 2.85 (t, 2H), 3.70 (s, 3H), 4.15 (t, 2H), 4.55 (t, 2H), 4.8 (t, 2H), 6.9–7.0 (m, 1H), 7.02–7.12 (m, 5H), 7.15–7.20 (m, 1H), 7.2–7.3 (m, 1H), 8.4 (t, 1H), 12.0 (s, 1H).

Example 18 (166)

7-Fluoro-1,2-dihydro-5-[2,2-dimethyl-4-(1,3-dioxolanyl)methyl]-3-oxo-N-(2-fluorophenyl)pyrido[1,2-a]benzimidazole-4-carboxamide To a cooled (0° C.) and suspended solution of 10 (X=7-F, R'=2-FPh, 2.39 g, 7.00 mmol), triphenylphosphine (3.67 g, 14.0 mmol), 2,2-dimethyl-1,3-dioxolane-4-methanol (1.74 mL, 14.0. mmol) in CH₂Cl₂ (140 mL) was added DEAD (2.20 mL, 14.0 mmol) over a 15 min period. The reaction mixture was stirred for 44 h at room temperature and concentrated in vacuo to a brown solid. The crude product was twice chromatographed on silica gel (elution with 1:3 hexane/ethyl acetate) to provide 1.65 g of product. A sample of 0.40 g of this material was recrystallized from ethyl acetate/hexane to yield 0.24 g of 166 as a white fibrous solid. MS(Cl—NH₃) MH⁺=456. H-1 NMR (300 MHz, CDCl₃) δ 1.3 (s, 3H), 1.4 (s, 3H), 2.75–2.95 (m, 2H), 3.7–3.8 (m, 1H), 4.1–4.25 (m, 3H), 4.3–4.4 (m, 1H), 4.6–4.7 (m, 1H), 4.75–4.85 (m, 1H), 6.9–7.05 (m, 1H), 7.1–7.2 (m, 3H), 7.2–7.25 (m, 1H). 7.55–7.60 (m, 1H), 5.35 (t, 1H) 12.1 (s, 1H).

Example 19 (162)

7-Fluoro-1,2-dihydro-5-[2,3-dihydroxypropyl]-3-oxo-N-(2-fluorophenyl)pyrido[1,2-a]benzimidazole-4-carboxamide A solution of 166 (1.71 g, 3.75 mmol), and p-toluenesulfonic acid monohydrate (0.20 g, 1.05 mmol) in methanol (60 mL) was heated to reflux for 18 h. The reaction mixture was concentrated in vacuo, dissolved in CHCl₃ (150 mL), and neutralized with aqueous Na₂CO₃. The CHCl₃ solution was dried over Na₂SO₄, filtered and concentrated to a yellow flakey solid. Purification of the crude product was achieved by column chromatography on silica gel (6:94 MeOH/CHCl₃) and subsequent recrystallization from ethyl acetate/hexane provided 0.64 g (39%) of 162 as a white amorphous solid. MS(Cl—NH₃) MH⁺=416. H-1 NMR (300 MHz, CDCl₃) δ 2.6–2.8 (m, 2H), 3.3–3.4 (m, 2H), 3.8–3.9 (m, 1H), 4.25–4.40 (m, 3H), 4.65–4.75 (m, 2H, 1 exchangeable H), 4.9 (br s, 1H, 1 exchangeable H), 6.95–7.05 (m, 1H), 7.1–7.2 (m, 1H), 7.2–7.3 (m, 2H), 7.55–7.65 (m, 2H), 8.45 (t, 1H), 12.25 (s, 1H).

Example 20 (38)

7-Fluoro-1,2-dihydro-5-[N-(2-(methoxy)ethyl)-2-(methylamino)ethyl]-3-oxo-N-(2-fluorophenyl) pyrido[1,2-a]-benzimidazole-4-carboxamide To a cooled (0° C.) solution of 52 (0.54 g, 1.25 mmol), and 37% aqueous formaldehyde (0.30 mL, 3.70 mmol) in methanol (20 mL) was added sodium borohydride (237 mg, 6.26 mmol). The reaction was stirred at room temperature for 2 h. At 1 h intervals, 0.30 and 0.20 mL quantities of aq. HCHO and 243 and 125 mg quantities of sodium borohydride were added to the reaction mixture. After a total of 5 h, the reaction was partitioned between aq. NaCl and CHCl₃ (70 mL), the aqueous phase was extracted with additional CHCl₃ (2×70 mL). The combined CHCl₃ solution was dried (Na₂SO₄), filtered, and concentrated in vacuo and the crude product was chromatographed on silica gel (3:97 methanol/chloroform) to provide 0.44 g of pure product. This free base was dissolved in methanol (25 ml), filtered, and acidified with concentrated HCl in isopropanol to a pH of 4.0 to give the HCl salt of 38 (250 mg, 40%) as a white powder. MS(Cl—NH₃) MH⁺=457. H-1 NMR (300 MHz, DMSO-d₆) δ 2.75 (t, 2H), 2.9 (d, 3H), 3.30–3.55 (m, 5H), 3.7–3.9 (m, 4H), 4.3 (t, 2H), 4.7 (t, 2H), 6.9–7.0 (m, 1H), 7.1 (t, 1H), 7.2–7.4 (m, 3H), 7.75–7.80 (m, 1H), 7.9–8.0 (m, 1H), 8.5 (t, 1H), 10.8 (br s, 1H), 12.4 (s, 1H).

Example 21 (94)

6-Hydroxy-1,2-dihydro-5-(2-hydroxyethyl)-3-oxo-N-(2-fluorophenyl)pyrido[1,2-a]benzimidazole-4-carboxamide A solution of 96 (0.25 g, 0.61 mmol) in dichloromethane (3 mL) was slowly added to a solution of boron tribromide (1.0M in dichloromethane, 3.0 mL, 3.0 mmol) at 0° C. The resulting mixture was stirred at room temperature for 22 hrs. An additional 10 mL of dichloromethane was added to the mixture followed by 2 mL of isopropanol. The resultant solution was washed with a saturated solution of aqueous sodium bicarbonate (10 mL). The organic layer was separated, and methanol was added until the layer became a clear solution. The solution was dried over sodium sulfate, and the solvent was evaporated in vacuo. The residue was triturated in hot ethanol, and the product was collected by filtration and dried in vacuo to give a colorless solid of 94 (0.13 g, 56%) mp 214°–216° C.; MS m/z 384 (MH⁺). H-1 NMR (DMSO-d₆) δ 2.65 (t, 2H), 3.58 (t, 2H), 4.24 (t, 2H), 4.70 (t, 2H), 6.78 (d, 1H), 6.93–7.02 (m, 1H), 7.09–7.28 (m, 4H), 8.50 (t, 1H), 12.35 (br s, 1H).

TABLE 4

Physical Properties of N-5 Nitrogen Containing PBI Derivatives.

| | | Elemental Analysis Data | | | | | |
|---|---|---|---|---|---|---|---|
| | | Found | | | Calculated | | |
| Cp # | mp °C. | C | H | N | C | H | N | empirical formula |
| 32 | 233–240 | 56.34 | 4.38 | 15.45 | 56.29 | 4.44 | 15.75 | $C_{25}H_{22}F_2N_6O_3 \cdot HCl \cdot 0.25H_2O$ |
| 33 | 177–184 | 56.49 | 5.63 | 15.09 | 56.88 | 5.69 | 15.31 | $C_{26}H_{28}F_2N_6O_2 \cdot HCl \cdot H_2O$ |
| 34 | 176–180 | 49.37 | 5.48 | 14.33 | 49.61 | 5.75 | 14.46 | $C_{20}H_{23}N_5O_3S \cdot 1.3HCl \cdot 1.25H_2O$ |
| 35 | 231(dec) | 47.05 | 3.25 | 10.78 | 46.33 | 3.50 | 10.81 | $C_{20}H_{18}F_4N_4O_4S_2$ |
| 36 | 240.5–242 | 60.51 | 4.07 | 15.23 | 60.71 | 4.30 | 15.39 | $C_{23}H_{19}F_2N_5O_3 \cdot 0.2H_2O$ |
| 37 | 197.5–199 | 49.10 | 3.58 | 10.28 | 49.39 | 3.58 | 10.47 | $C_{22}H_{19}F_5N_4O_4S \cdot O.25H_2O$ |
| 38 | 200–205 | 58.35 | 5.70 | 11.27 | 58.05 | 5.56 | 11.28 | $C_{24}H_{26}F_2N_4O_3 \cdot HCl \cdot 0.2H_2O$ |
| 39 | 229–230.8 | 53.97 | 3.44 | 9.34 | 53.91 | 3.52 | 9.31 | $C_{27}H_{21}F_5N_4O_4S \cdot 0.5H_2O$ |
| 40 | 200–202 | 59.21 | 4.82 | 13.25 | 59.31 | 4.98 | 13.30 | $C_{23}H_{23}F_2N_5O_2$ |
| 41 | 218–220 | 56.39 | 5.66 | 11.34 | 56.38 | 5.76 | 11.43 | $C_{23}H_{24}F_2N_4O_2$ |
| 42 | >200 | 60.40 | 4.19 | 9.52 | 60.43 | 3.80 | 10.07 | $C_{28}H_{21}F_5N_4O_3$ |
| 43 | 256–257 | 56.62 | 4.98 | 11.83 | 56.78 | 4.98 | 12.04 | $C_{22}H_{22}ClFN_4O_2$ |
| 44 | 169–171 | 59.41 | 4.22 | 10.62 | 59.54 | 4.23 | 10.68 | $C_{26}H_{22}F_2N_4O_4S$ |
| 45 | 243–244 | 58.06 | 5.17 | 12.16 | 58.39 | 5.21 | 12.33 | $C_{22}H_{22}F_2N_4O_2$ |
| 46 | 195–197 | 62.21 | 4.58 | 11.28 | 65.19 | 4.46 | 11.26 | $C_{27}H_{22}F_2N_4O_3$ |
| 47 | 188–191 | 54.29 | 3.88 | 10.64 | 54.33 | 3.80 | 10.56 | $C_{24}H_{20}F_2N_4O_4S_2$ |
| 48 | >200 | 48.86 | 3.32 | 10.70 | 48.84 | 3.32 | 10.85 | $C_{21}H_{17}F_5N_4O_4S$ |
| 49 | 185–190 | 52.73 | 5.25 | 11.82 | 52.80 | 5.32 | 12.31 | $C_{20}H_{21}FN_4O_2S$ |
| 50 | 200–201 | 54.16 | 4.10 | 11.87 | 54.54 | 4.36 | 12.11 | $C_{21}H_{20}F_2N_4O_4S \cdot 0.25H_2O$ |
| 51 | >200 | 54.89 | 3.56 | 11.52 | 55.01 | 3.57 | 11.66 | $C_{22}H_{17}F_5N_4O_3$ |
| 52 | 191–194 | 56.54 | 5.41 | 11.32 | 56.61 | 5.37 | 11.47 | $C_{23}H_{24}F_2N_4O_3 \cdot HCl \cdot 0.5H_2O$ |
| 53 | 189–191 | 61.99 | 4.67 | 13.09 | 61.97 | 4.70 | 13.14 | $C_{22}H_{20}F_2N_4O_3$ |
| 54 | 203–207 | 58.94 | 4.50 | 12.28 | 58.93 | 4.50 | 12.49 | $C_{22}H_{20}F_4N_4O_2$ |
| 55 | 155–157 | 61.01 | 4.83 | 12.82 | 61.39 | 4.92 | 13.01 | $C_{22}H_{21}F_3N_4O_2$ |
| 56 | 203–205 | 61.75 | 5.64 | 9.48 | 61.85 | 5.62 | 9.62 | $C_{30}H_{30}F_2N_4O_3 \cdot HCl \cdot 0.75H_2O$ |
| 57 | 217–219 | 61.30 | 4.60 | 14.00 | 61.06 | 4.61 | 14.24 | $C_{20}H_{18}F_2N_4O_2 \cdot 0.5H_2O$ |
| 58 | 226–228 | 62.01 | 5.29 | 11.43 | 61.98 | 5.41 | 11.56 | $C_{25}H_{28}F_2N_4O_4$ |
| 59 | 208–212 | 56.36 | 5.03 | 12.62 | 56.25 | 5.06 | 12.49 | $C_{21}H_{20}F_2N_4O_2 \cdot HCl \cdot 0.75H_2O$ |
| 60 | 227–227.8 | 60.88 | 3.62 | 10.83 | 61.18 | 3.55 | 10.98 | $C_{28}H_{18}F_4N_4O_3$ |
| 61 | 251–251.8 | 63.15 | 3.83 | 11.12 | 63.41 | 3.89 | 11.38 | $C_{26}H_{19}F_3N_4O_3$ |
| 62 | 224.7–225 | 59.31 | 4.84 | 9.86 | 59.00 | 5.13 | 9.83 | $C_{28}H_{25}F_3N_4O_2 \cdot HCl \cdot 1.5H_2O$ |
| 63 | 195–195.5 | 63.48 | 5.55 | 8.21 | 63.68 | 5.34 | 8.49 | $C_{34}H_{29}F_3N_4O_2 \cdot HCl \cdot 0.5H_2O \cdot MeOH$ |
| 64 | 197–197.7 | 59.88 | 4.73 | 8.02 | 59.78 | 4.87 | 8.20 | $C_{34}H_{30}F_2N_4O_2 \cdot HClO_4 \cdot H_2O$ |
| 65 | 216.4–217 | 59.22 | 4.20 | 9.94 | 59.00 | 4.60 | 9.83 | $C_{28}H_{24}F_4N_4O_2 \cdot HCl \cdot 0.5H_2O$ |
| 66 | 233–233.5 | 57.01 | 5.17 | 11.51 | 57.44 | 5.03 | 11.65 | $C_{23}H_{23}F_3N_4O_2 \cdot HCl$ |
| 67 | 231.5–232 | 58.82 | 5.54 | 11.86 | 58.54 | 5.55 | 11.87 | $C_{23}H_{24}F_3N_4O_2 \cdot HCl \cdot 0.5H_2O$ |
| 68 | 230–232.5 | 59.08 | 5.75 | 10.63 | 58.70 | 5.87 | 10.53 | $C_{26}H_{29}F_3N_4O_2 \cdot HCl \cdot 0.5H_2O$ |
| 69 | 236–238.5 | 60.10 | 6.14 | 10.75 | 59.71 | 6.17 | 10.71 | $C_{26}H_{30}F_2N_4O_2 \cdot HCl \cdot H_2O$ |
| 70 | 219–221.5 | 57.99 | 5.37 | 11.00 | 58.24 | 5.29 | 11.32 | $C_{24}H_{25}F_3N_4O_2 \cdot HCl$ |
| 71 | 219–221.5 | 57.67 | 5.86 | 11.16 | 57.20 | 5.60 | 11.11 | $C_{24}H_{26}F_2N_4O_2 \cdot HCl \cdot 1.5H_2O$ |
| 72 | 225–227 | 54.25 | 6.11 | 14.96 | 53.85 | 5.81 | 14.95 | $C_{21}H_{23}N_5O_2 \cdot 2HCl \cdot H_2O$ |
| 73 | 222–226 | 56.10 | 4.70 | 11.89 | 56.05 | 4.81 | 11.88 | $C_{22}H_{21}F_3N_4O_2 \cdot HCl \cdot 0.25H_2O$ |
| 74 | 227–229 | 58.09 | 5.16 | 12.22 | 58.28 | 5.22 | 12.36 | $C_{22}H_{22}F_2N_4O \cdot HCl \cdot 0.25H_2O$ |
| 75 | 180–182.3 | 60.43 | 3.86 | 10.05 | 60.43 | 3.80 | 10.07 | $C_{28}H_{21}F_5N_4O_3$ |
| 76 | >200 | 60.40 | 3.81 | 9.90 | 60.43 | 3.80 | 10.07 | $C_{28}H_{21}F_5N_4O_3$ |
| 77 | 179.8–180 | 62.42 | 4.69 | 17.05 | 62.57 | 4.63 | 17.17 | $C_{17}H_{15}FN_4O_2$ |
| 78 | >200 | 64.58 | 5.62 | 15.09 | 64.42 | 5.68 | 15.02 | $C_{20}H_{21}FN_4O_2$ |
| 79 | >200 | 60.04 | 5.62 | 14.77 | 60.24 | 5.27 | 14.64 | $C_{24}H_{25}F_2N_5O_3 \cdot 0.5H_2O$ |
| 80 | 114–116.1 | 62.87 | 5.88 | 12.58 | 62.92 | 6.01 | 12.65 | $C_{29}H_{33}F_2N_5O_4$ |
| 81 | 98–100.5 | 61.48 | 5.45 | 14.86 | 61.73 | 5.40 | 15.00 | $C_{24}H_{25}F_2N_5O_2$ |
| 82 | >200 | 63.88 | 4.30 | 14.21 | 63.55 | 4.32 | 14.12 | $C_{24}H_{25}F_2N_3O_4 \cdot 0.25H_2O$ |
| 83 | 187–188.2 | 66.17 | 4.77 | 10.83 | 66.39 | 4.97 | 11.06 | $C_{28}H_{25}F_3N_4O_2$ |
| 84 | 153–153.4 | 66.68 | 5.20 | 11.48 | 68.84 | 5.36 | 11.47 | $C_{28}H_{26}F_2N_4O$ |
| 85 | 200–206 | 66.37 | 3.79 | 10.97 | 66.49 | 3.99 | 11.08 | $C_{21}H_{15}F_2N_3O_2$ |
| 86 | 183–202 | 58.78 | 4.95 | 10.31 | 59.04 | 5.07 | 10.59 | $C_{24}H_{25}F_2N_3O_4 \cdot 0.5C_4H_4O_4 \cdot 0.8H_2O$ |
| 87 | 189–200.5 | 59.48 | 5.04 | 9.51 | 59.69 | 5.01 | 9.60 | $C_{24}H_{24}F_2N_4O_2 \cdot 1.25C4H4O4$ |
| 88 | 223.2–224 | 63.44 | 5.30 | 12.33 | 63.43 | 5.32 | 12.33 | $C_{24}H_{24}F_2N_4O_3$ |
| 89 | 272–274 | 62.03 | 3.78 | 14.30 | 62.08 | 3.71 | 14.41 | $C_{20}H_{14}F_2N_4O_2$ |
| 90 | >206 | 67.14 | 4.87 | 15.04 | 67.37 | 4.85 | 14.96 | $C_{21}H_{18}N_4O_3$ |
| 91 | 224–226 | 62.69 | 5.39 | 8.22 | 62.77 | 5.07 | 8.45 | $C_{26}H_{25}F_2N_3O_5$ |
| 92 | 113–115 | 66.28 | 5.02 | 8.29 | 66.53 | 4.98 | 8.31 | $C_{28}H_{25}F_2N_3O_4$ |
| 93 | 104–106 | 60.80 | 5.35 | 8.85 | 60.88 | 5.32 | 8.87 | $C_{24}H_{25}F_2N_3O_5$ |
| 94 | 214–216 | 61.85 | 4.61 | 10.60 | 61.93 | 4.81 | 10.83 | $C_{20}H_{18}FN_3O_4 \cdot 0.25H_2O$ |
| 95 | 146–156 | 63.46 | 5.74 | 8.96 | 63.01 | 5.51 | 9.19 | $C_{24}H_{25}F_2N_3O_4$ |
| 96 | 219–221 | 63.90 | 5.28 | 10.14 | 64.22 | 5.39 | 10.21 | $C_{22}H_{22}FN_3O_4$ |
| 97 | 148–150 | 61.45 | 4.59 | 9.73 | 61.53 | 4.93 | 9.78 | $C_{22}H_{21}F_2N_3O_4$ |
| 98 | 198–200 | 59.30 | 5.24 | 14.57 | 59.17 | 5.32 | 14.48 | $C_{19}H_{20}N_4O_3S$ |
| 99 | 200–203 | 60.61 | 4.53 | 9.77 | 60.72 | 4.61 | 10.12 | $C_{21}H_{19}F_2N_3O_4$ |
| 100 | 165–166 | 58.30 | 4.57 | 8.73 | 58.35 | 4.47 | 8.88 | $C_{23}H_{21}F_2N_3O_6$ |
| 101 | 124–126 | 62.36 | 5.48 | 10.93 | 62.64 | 5.52 | 10.96 | $C_{20}H_{21}N_3O_3S$ |
| 102 | 201–202 | 58.30 | 4.90 | 14.79 | 55.81 | 3.81 | 16.27 | $C_{18}H_{18}N_4O_3S$ |

TABLE 4-continued

Physical Properties of N-5 Nitrogen Containing PBI Derivatives.

| | | Found | | | Calculated | | | |
|---|---|---|---|---|---|---|---|---|
| Cp # | mp °C. | C | H | N | C | H | N | empirical formula |
| 103 | 168–169 | 60.24 | 4.29 | 10.08 | 60.43 | 4.35 | 10.07 | $C_{21}H_{18}F_3N_3O_3$ |
| 104 | 143.5–146 | 64.00 | 5.40 | 10.16 | 64.23 | 5.39 | 10.21 | $C_{22}H_{22}FN_3O_4$ |
| 105 | 164.5–167 | 61.61 | 5.28 | 11.33 | 61.77 | 5.18 | 11.37 | $C_{19}H_{19}N_3O_3S$ |
| 106 | 178–179.1 | 62.51 | 5.37 | 9.83 | 62.18 | 5.22 | 9.89 | $C_{22}H_{22}FN_3O_4$ |
| 107 | 145–147.3 | 64.58 | 6.61 | 10.78 | 64.35 | 6.69 | 10.72 | $C_{22}H_{27}FN_3O_3$ |
| 108 | 151–153.3 | 67.29 | 6.53 | 8.91 | 65.10 | 6.76 | 10.85 | $C_{21}H_{26}FN_3O_3$ |
| 109 | 143–145.2 | 60.92 | 5.62 | 12.18 | 60.24 | 5.62 | 11.71 | $C_{18}H_{20}FN_3O_3$ |
| 110 | 202–204 | 60.11 | 4.42 | 9.98 | 60.43 | 4.35 | 10.07 | $C_{21}H_{18}F_3N_3O_3$ |
| 111 | 211–212 | 57.28 | 3.76 | 9.46 | 57.70 | 3.96 | 9.61 | $C_{21}H_{17}F_4N_3O_3$ |
| 112 | 158–159 | 63.12 | 4.59 | 9.47 | 63.14 | 4.61 | 9.59 | $C_{23}H_{20}FN_3O_3S$ |
| 113 | 176–176.6 | 65.80 | 5.11 | 9.89 | 65.85 | 5.05 | 10.02 | $C_{23}H_{21}N_3O_3S$ |
| 114 | 116–118 | 59.62 | 4.17 | 9.44 | 59.59 | 4.32 | 9.48 | $C_{22}H_{19}F_2N_3O_5$ |
| 115 | 184–185 | 63.86 | 4.95 | 9.23 | 63.84 | 4.91 | 9.31 | $C_{24}H_{22}FN_3O_3S$ |
| 116 | 148.7–149 | 61.84 | 5.78 | 12.29 | 61.79 | 5.76 | 12.01 | $C_{18}H_{20}FN_3O_3 \cdot 0.25H_2O$ |
| 117 | 200–202 | 61.97 | 4.37 | 9.84 | 61.82 | 4.48 | 9.83 | $C_{22}H_{19}F_2N_3O_4$ |
| 118 | 211–218 | 49.27 | 4.05 | 8.22 | 49.18 | 4.31 | 8.31 | $C_{20}H_{20}FN_3O_5S_2$ |
| 119 | 201–205 | 52.58 | 4.37 | 8.62 | 52.60 | 4.62 | 8.76 | $C_{21}H_{22}FN_3O_5S_2$ |
| 120 | 158.4–159 | 56.62 | 4.29 | 10.31 | 56.50 | 4.49 | 10.40 | $C_{19}H_{18}ClN_3O_3S$ |
| 121 | 141–143 | 60.44 | 4.05 | 10.10 | 60.43 | 4.35 | 10.07 | $C_{21}H_{18}F_3N_3O_3$ |
| 122 | 80–84 | 58.01 | 4.32 | 11.16 | 58.23 | 4.63 | 10.72 | $C_{19}H_{18}FN_3O_3S \cdot 0.25H_2O$ |
| 123 | 182–183.5 | 54.46 | 4.39 | 9.48 | 54.55 | 4.35 | 9.54 | $C_{20}H_{19}ClFN_3O_3S \cdot 0.25H_2O$ |
| 124 | 73–74.5 | 59.52 | 5.04 | 10.41 | 59.84 | 5.02 | 10.47 | $C_{20}H_{20}FN_3O_3S$ |
| 125 | 168–170 | 57.85 | 3.92 | 9.54 | 57.93 | 3.94 | 9.65 | $C_{21}H_{17}F_4N_3O_3$ |
| 126 | 182–185 | 60.08 | 4.36 | 9.97 | 60.43 | 4.35 | 10.07 | $C_{21}H_{18}F_3N_3O_3$ |
| 127 | 192–195 | 52.93 | 3.87 | 9.58 | 52.96 | 3.98 | 9.75 | $C_{19}H_{17}ClFN_3O_3S$ |
| 128 | 177–179 | 58.80 | 4.60 | 10.61 | 58.90 | 4.68 | 10.85 | $C_{19}H_{18}FN_3O_3S$ |
| 129 | 170–173 | 58.72 | 4.61 | 13.07 | 59.08 | 4.49 | 13.12 | $C_{21}H_{20}F_2N_4O_3$ |
| 130 | 126–127.2 | 60.53 | 5.21 | 10.05 | 60.71 | 5.34 | 10.11 | $C_{21}H_{22}FN_3O_3S$ |
| 131 | 148–149.5 | 55.04 | 4.35 | 9.39 | 55.11 | 4.39 | 9.64 | $C_{20}H_{19}ClFN_3O_3S$ |
| 132 | 150–150.8 | 59.78 | 5.04 | 10.42 | 59.84 | 5.02 | 10.47 | $C_{20}H_{20}FN_3O_3S$ |
| 133 | 133.5–135 | 54.21 | 4.01 | 9.85 | 54.09 | 4.06 | 9.96 | $C_{19}H_{17}ClFN_3O_3S$ |
| 134 | 161.5–166 | 50.95 | 3.95 | 9.30 | 50.90 | 4.05 | 9.37 | $C_{19}H_{18}BrN_3O_3S$ |
| 135 | 190–198 | 60.33 | 4.35 | 9.96 | 60.43 | 4.35 | 10.07 | $C_{21}H_{18}F_3N_3O_3$ |
| 136 | 129–136 | 61.05 | 4.91 | 9.31 | 61.05 | 4.91 | 9.31 | $C_{22}H_{20}F_3N_3O_3$ |
| 137 | 215–216 | 54.03 | 3.89 | 9.88 | 54.09 | 4.06 | 9.96 | $C_{19}H_{17}ClFN_3O_3S$ |
| 138 | 170–171 | 58.83 | 4.74 | 10.71 | 58.90 | 4.69 | 10.85 | $C_{19}H_{18}FN_3O_3S$ |
| 139 | 194–196 | 55.35 | 4.26 | 14.53 | 55.66 | 4.41 | 14.42 | $C_{18}H_{17}FN_4O_3S$ |
| 140 | 136–137 | 56.73 | 4.71 | 13.88 | 56.71 | 4.76 | 13.92 | $C_{19}H_{19}FN_4O_3S$ |
| 141 | 146–157 | 62.46 | 5.39 | 10.89 | 62.64 | 5.52 | 10.96 | $C_{20}H_{21}N_3O_3S$ |
| 142 | 164–166 | 59.62 | 4.87 | 10.36 | 59.84 | 5.02 | 10.47 | $C_{20}H_{20}FN_3O_3S$ |
| 143 | 178–179 | 48.99 | 3.45 | 8.88 | 48.94 | 3.67 | 9.01 | $C_{19}H_{17}BrFN_3O_3S$ |
| 144 | 195–197 | 54.07 | 3.96 | 10.00 | 54.09 | 4.06 | 9.96 | $C_{19}H_{17}ClFN_3O_3S$ |
| 145 | 190–192 | 56.65 | 4.47 | 10.41 | 56.50 | 4.49 | 10.40 | $C_{19}H_{18}ClN_3O_3S$ |
| 146 | 173–175 | 60.44 | 4.58 | 10.08 | 60.65 | 4.61 | 10.10 | $C_{21}H_{19}ClFN_3O_3$ |
| 147 | 156–159 | 58.65 | 4.23 | 9.46 | 58.80 | 4.26 | 9.35 | $C_{22}H_{19}F_4N_3O_3$ |
| 148 | 203–204 | 60.25 | 4.32 | 9.97 | 60.43 | 4.35 | 10.07 | $C_{21}H_{18}F_3N_3O_3$ |
| 149 | 147–148.4 | 64.76 | 5.39 | 9.58 | 64.63 | 5.42 | 9.83 | $C_{23}H_{23}F_2N_3O_3$ |
| 150 | 187–188.8 | 63.24 | 4.75 | 10.47 | 63.15 | 4.80 | 10.52 | $C_{21}H_{19}F_2N_3O_3$ |
| 151 | 109.5–111 | 64.55 | 5.40 | 9.93 | 64.63 | 5.42 | 9.83 | $C_{23}H_{23}F_2N_3O_3$ |
| 152 | 168–170.4 | 65.79 | 5.23 | 10.90 | 66.13 | 5.29 | 11.02 | $C_{21}H_{20}FN_3O_3$ |
| 153 | 118–122 | 63.58 | 5.72 | 8.86 | 63.68 | 5.77 | 8.91 | $C_{25}H_{27}F_2N_3O_4$ |
| 154 | 210–212 | 55.51 | 4.38 | 14.54 | 55.66 | 4.41 | 14.42 | $C_{18}H_{17}FN_4O_3S$ |
| 155 | 168–169 | 63.31 | 5.06 | 10.43 | 63.40 | 5.07 | 10.56 | $C_{21}H_{20}ClN_3O_3$ |
| 156 | 173–175 | 60.42 | 4.50 | 9.98 | 60.65 | 4.60 | 10.11 | $C_{21}H_{19}ClFN_3O_3$ |
| 157 | 212–215 | 62.24 | 4.53 | 11.08 | 62.34 | 4.45 | 10.90 | $C_{20}H_{17}F_2N_3O_3$ |
| 158 | 125–127 | 61.53 | 4.76 | 9.69 | 61.53 | 4.93 | 9.79 | $C_{22}H_{21}F_2N_3O_4$ |
| 159 | 118–120 | 63.84 | 5.06 | 10.29 | 63.92 | 5.12 | 10.16 | $C_{22}H_{21}F_2N_3O_3$ |
| 160 | 142–145 | 60.13 | 4.87 | 9.47 | 60.41 | 4.84 | 9.61 | $C_{21}H_{19}F_2N_3O_4$ |
| 161 | 152–155.1 | 62.92 | 4.59 | 10.62 | 63.15 | 4.80 | 10.52 | $C_{21}H_{19}F_2N_3O_3$ |
| 162 | 202–204 | 63.16 | 4.98 | 9.22 | 63.29 | 5.09 | 9.23 | $C_{24}H_{23}F_2N_3O_4$ |
| 163 | 79–93 | 63.74 | 4.99 | 11.74 | 63.73 | 5.14 | 11.43 | $C_{26}H_{23}FN_4O_3$ |
| 164 | 191–193.6 | 56.54 | 5.41 | 11.32 | 56.61 | 5.37 | 11.47 | $C_{23}H_{24}F_2N_4O_3 \cdot HCl \cdot 0.5H_2O$ |
| 165 | 141–144 | 62.20 | 5.25 | 9.36 | 62.30 | 5.23 | 9.48 | $C_{23}H_{23}F_2N_3O_4$ |
| 166 | 203–205 | 61.75 | 5.64 | 9.48 | 61.85 | 5.62 | 9.62 | $C_{30}H_{30}F_2N_4O_3 \cdot HCl \cdot 0.75H_2O$ |
| 167 | 198–200 | 67.56 | 4.51 | 8.94 | 67.67 | 4.59 | 9.11 | $C_{26}H_{21}F_2N_3O_3$ |
| 168 | 213–217 | 62.05 | 4.29 | 10.83 | 62.34 | 4.45 | 10.90 | $C_{20}H_{17}F_2N_3O_3$ |
| 169 | 184–187 | 63.19 | 4.65 | 10.25 | 63.15 | 4.80 | 10.52 | $C_{21}H_{19}F_2N_3O_3$ |
| 170 | 113–115 | 68.57 | 5.12 | 8.51 | 68.70 | 5.15 | 8.58 | $C_{28}H_{25}F_2N_3O_3$ |
| 171 | 157–158 | 68.07 | 4.79 | 8.89 | 68.20 | 4.88 | 8.84 | $C_{27}H_{23}F_2N_3O_3$ |
| 172 | 144–145.5 | 62.81 | 5.14 | 10.43 | 63.15 | 4.80 | 10.52 | $C_{21}H_{19}F_2N_3O_3$ |
| 173 | 178–185 | 60.06 | 4.30 | 9.93 | 60.43 | 4.35 | 10.07 | $C_{21}H_{18}F_3N_3O_3$ |

TABLE 4-continued

Physical Properties of N-5 Nitrogen Containing PBI Derivatives.

| | | Found | | | Calculated | | | |
|---|---|---|---|---|---|---|---|---|
| Cp # | mp °C. | C | H | N | C | H | N | empirical formula |
| 174 | 170–171 | 64.96 | 5.06 | 9.75 | 64.93 | 4.98 | 9.88 | $C_{23}H_{21}F_2N_3O_3$ |
| 175 | >200 | 64.46 | 4.73 | 9.77 | 64.93 | 4.98 | 9.88 | $C_{23}H_{21}F_2N_3O_3$ |
| 176 | 206–207 | 63.21 | 4.99 | 9.15 | 63.29 | 5.09 | 9.23 | $C_{24}H_{23}F_2N_3O_4$ |
| 177 | 220–223 | 59.62 | 3.80 | 10.34 | 59.88 | 3.82 | 10.47 | $C_{20}H_{15}F_2N_3O_4 \cdot 0.1H_2O$ |
| 178 | 219–221 | 65.59 | 5.28 | 9.56 | 65.43 | 5.16 | 9.45 | $C_{24}H_{23}F_2N_3O_3$ |
| 179 | 210–215 | 58.25 | 3.88 | 9.99 | 58.07 | 3.43 | 10.03 | $C_{27}H_{19}F_5N_4O_4$ |
| 180 | 206–208 | 64.67 | 4.99 | 9.75 | 64.93 | 4.98 | 9.88 | $C_{23}H_{21}F_2N_3O_3$ |
| 181 | 224–228 | 61.40 | 4.46 | 9.67 | 61.82 | 4.48 | 9.83 | $C_{22}H_{19}F_2N_3O_4$ |
| 182 | 195–196 | 60.73 | 4.64 | 10.05 | 60.71 | 4.61 | 10.11 | $C_{21}H_{19}F_2N_3O_2S$ |
| 183 | 218–220 | 58.11 | 4.42 | 9.65 | 58.46 | 4.44 | 9.74 | $C_{21}H_{19}F_2N_3O_3S$ |

TABLE 1

Biological Activity of N-5 Nitrogen-Containing Derivatives.

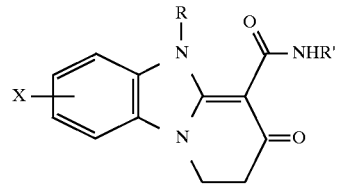

| Cp # | R' | R | X | GABA$_A$ Receptor Binding IC$_{50}$ (nM) | Mouse Metrazol (ED$_{50}$, mg/kg) ip | Mouse Metrazol po | Rat Conflict (MED, mg/kg) ip | Rat Conflict po | Squirrel Monkey Conflict (mg/kg, po) |
|---|---|---|---|---|---|---|---|---|---|
| 32 | 2-FPh | —CH$_2$C(O)NHCH$_2$CH$_2$(4-imidazolyl) | 7-F | 3.56 | — | — | — | >3 | — |
| 33 | 2-FPh | —(CH$_2$)$_2$NHC(=NMe)—N-pyrrolidinyl | 7-F | 54 | — | — | — | >3 | — |
| 34 | 2-thiazolyl | —CH$_2$CH$_2$NMe$_2$ | 6-MeO | 1003 | — | — | — | >3 | — |
| 35 | 2-[(5-Me)thienyl] | —CH$_2$CH$_2$NHSO$_2$CF$_3$ | 7-F | 46.9 | — | — | — | >10 | — |
| 36 | 2-FPh | —CH$_2$C(O)NHCH$_2$CH$_2$CN | 7-F | 3.3 | >1 | >30 | — | >10 | — |
| 37 | 2-FPh | —CH$_2$CH$_2$N(Me)SO$_2$CF$_3$ | 7-F | 18.3 | >1 | >30 | — | >10 | — |
| 38 | 2-FPh | —(CH$_2$)$_2$N(Me)CH$_2$CH$_2$OMe | 7-F | 4.06 | <1 | 1 | — | 3 | — |
| 39 | 2-FPh | —CH$_2$CH$_2$NHSO$_2$(4-CF$_3$Ph) | 7-F | 122 | >1 | >3 | — | >10 | — |
| 40 | 2-FPh | —CH$_2$CH$_2$N=CHNMe$_2$ | 7-F | 35 | <1 | ca. 30 | — | 10 | — |
| 41 | 2-FPh | —CH$_2$CH$_2$N(Me)Et | 7-F | 9.8 | 3 | ca. 10 | — | 10 | — |
| 42 | 2-FPh | —CH$_2$CH$_2$NHC(O)(4-CF$_3$Ph) | 7-F | 17.0 | >30 | >30 | ≦10 | ca. 3 | — |
| 43 | 2-FPh | —CH$_2$CH$_2$NMe$_2$ | 7-Cl | 26.9 | 1–10 | <30 | 10 | >10 | — |
| 44 | 2-FPh | —CH$_2$CH$_2$NHSO$_2$Ph | 7-F | 10.1 | ≦1 | <30 | >10 | >10 | — |
| 45 | 2-FPh | —CH$_2$CH$_2$NMe$_2$ | 6-F | 40.6 | 1 | 3–10 | >10 | 10 | — |
| 46 | 2-FPh | —CH$_2$CH$_2$NHC(O)Ph | 7-F | 6.1 | 1 | 30 | — | ca. 10 | — |
| 47 | 2-FPh | —CH$_2$CH$_2$NHSO$_2$(2-thienyl) | 7-F | 13.7 | 1 | 30 | >10 | — | — |
| 48 | 2-FPh | —CH$_2$CH$_2$NHSO$_2$CF$_3$ | 7-F | 30.2 | ≦1 | <30 | — | 10 | >10 |
| 49 | 2-thienyl | —CH$_2$CH$_2$NMe$_2$ | 7-F | 152 | 3 | ca 5 | >10 | ca. 10 | — |
| 50 | 2-FPh | —CH$_2$CH$_2$NHSO$_2$Me | 7-F | 7.7 | 1 | <30 | >10 | — | — |
| 51 | 2-FPh | —CH$_2$CH$_2$NHC(O)CF$_3$ | 7-F | 0.51 | 0.3 | 1 | ca. 10 | >10 | — |
| 52 | 2-FPh | —CH$_2$CH$_2$NHCH$_2$CH$_2$OMe | 7-F | 7.42 | 1 | 1 | ca. 10 | 10 | — |
| 53 | 2-FPh | —CH$_2$CH$_2$NHC(O)Me | 7-F | 5.47 | 7 | 30 | >10 | — | — |
| 54 | 2,4,6-F$_3$Ph | —CH$_2$CH$_2$NMe$_2$ | 7-F | 208 | 10 | >30 | >10 | >10 | — |
| 55 | 2,4-F$_2$Ph | —CH$_2$CH$_2$NMe$_2$ | 7-F | 31.8 | 1 | 1 | <10 | 3 | — |
| 56 | 2-FPh | —CH$_2$CH$_2$N(CH$_2$Ph)CH$_2$CH$_2$OMe | 7-F | 7.99 | 1 | ca. 10 | >10 | — | — |
| 57 | 2-FPh | —CH$_2$CH$_2$NH$_2$ | 7-F | 5.13 | 0.3 | 10 | ca. 10 | 10 | — |
| 58 | 2-FPh | —CH$_2$CH$_2$NHC(O)OtBu | 7-F | 0.54 | <1 | <30 | ≦10 | >10 | — |
| 59 | 2-FPh | —CH$_2$CH$_2$NHMe | 7-F | 16.0 | 3 | 10 | 10 | 1 | 3 |
| 60 | 2,6-F$_2$Ph | —CH$_2$C(O)NH(2-FPh) | 7-F | 21.4 | 10 | >30 | — | — | — |
| 61 | 2-FPh | —CH$_2$C(O)NH(2-FPh) | 7-F | 6.32 | <1 | 30 | >10 | — | — |
| 62 | 2-FPh | —CH$_2$CH$_2$N(Me)CH$_2$(4-FPh) | 7-F | 7.69 | 3 | 30 | <10 | >10 | — |
| 63 | 2,6-F$_2$Ph | —CH$_2$CH$_2$N(CH$_2$Ph)$_2$ | 7-F | 15.5 | — | — | >10 | — | — |
| 64 | 2-FPh | —CH$_2$CH$_2$N(CH$_2$Ph)$_2$ | 7-F | 3.02 | 3 | >30 | >10 | — | — |
| 65 | 2,6-F$_2$Ph | —CH$_2$CH$_2$N(Me)CH$_2$(4-FPh) | 7-F | 11.0 | >10 | >30 | >10 | — | — |
| 66 | 2,6-F$_2$Ph | —CH$_2$CH$_2$CH$_2$NMe$_2$ | 7-F | 83.7 | >30 | >10 | >10 | — | — |
| 67 | 2-FPh | —CH$_2$CH$_2$CH$_2$NMe$_2$ | 7-F | 3.29 | 3 | 30 | 10 | >10 | — |

TABLE 1-continued

Biological Activity of N-5 Nitrogen-Containing Derivatives.

| Cp # | R' | R | X | GABA$_A$ Receptor Binding IC$_{50}$ (nM) | Mouse Metrazol (ED$_{50}$, mg/kg) ip | Mouse Metrazol (ED$_{50}$, mg/kg) po | Rat Conflict (MED, mg/kg) ip | Rat Conflict (MED, mg/kg) po | Squirrel Monkey Conflict (mg/kg, po) |
|---|---|---|---|---|---|---|---|---|---|
| 68 | 2,6-F$_2$Ph | —CH$_2$CH$_2$N(iPr)$_2$ | 7-F | 44.6 | >10 | >30 | 10 | — | — |
| 69 | 2-FPh | —CH$_2$CH$_2$N(iPr)$_2$ | 7-F | 78.4 | 1 | >30 | >10 | — | — |
| 70 | 2,6-F$_2$Ph | —CH$_2$CH$_2$NEt$_2$ | 7-F | 267 | >10 | >30 | >10 | — | — |
| 71 | 2-FPh | —CH$_2$CH$_2$NEt$_2$ | 7-F | 74.5 | 2 | 10 | <10 | >10 | — |
| 72 | 4-pyridyl | —CH$_2$CH$_2$NMe$_2$ | H | 3840 | >10 | >30 | >10 | — | — |
| 73 | 2,6-F$_2$Ph | —CH$_2$CH$_2$NMe$_2$ | 7-F | 32.1 | >10 | >30 | >10 | — | — |
| 74 | 2-FPh | —CH$_2$CH$_2$NMe$_2$ | 7-F | 49.9 | 0.5 | <3 | <10 | 3 | ca. 2 |
| 75 | 2-FPh | —CH$_2$CH$_2$NHC(O)(3-CF$_3$)Ph | 7-F | 9.50 | >1 | >30 | — | >10 | — |
| 76 | 2-FPh | —CH$_2$CH$_2$NHC(O)(2-CF$_3$)Ph | 7-F | 40.9 | >1 | >30 | — | >10 | — |
| 77 | -cyclopropyl | —CH$_2$CN | 7-F | 0.86 | <1 | >30 | — | >10 | — |
| 78 | -cyclohexyl | —CH$_2$CN | 7-F | 30 | >1 | >30 | — | >10 | — |
| 79 | 2-FPh | —CH$_2$CH$_2$NHC(O)NHiPr | 7-F | 10.5 | >1 | >30 | — | >10 | — |
| 80 | 2-FPh | —(CH$_2$)$_2$—N(piperazine)N—C(O)tBu | 7-F | 3.7 | >1 | >30 | — | >10 | — |
| 81 | 2-FPh | —(CH$_2$)$_2$—N(piperazine)NH | 7-F | 12.7 | >1 | >30 | — | >10 | — |
| 82 | 4-(MeO)Ph | —CH$_2$CN | 7-F | 8.55 | <1 | >30 | — | >10 | — |
| 83 | 2,6-F$_2$Ph | —CH$_2$CH$_2$(4-Me$_2$N)Ph | 7-F | 36.2 | 3 | <30 | >10 | — | — |
| 84 | 2-FPh | —CH2CH2(4-Me2N)Ph | 7-F | 8.52 | 1 | <30 | >10 | — | — |
| 85 | 2-FPh | —CH$_2$CN | 7-F | 0.072 | 0.006 | 1 | <10 | 1 | >3 |
| 86 | 2,6-F$_2$Ph | piperidine-N—Me | 7-F | 26.3 | >10 | >30 | 10 | >10 | — |
| 87 | 2-FPh | piperidine-N—Me | 7-F | 30.7 | 3 | 10 | >10 | >10 | — |
| 88 | 2-FPh | —(CH$_2$)$_2$—N(morpholine)O | 7-F | 3.67 | 0.1 | 7 | >10 | 10 | — |
| 89 | 2-FPh | —CH$_2$CN | 7-F | 1.84 | <1 | 0.5 | — | 1 | — |
| 90 | 3-(MeO)Ph | —CH$_2$CN | H | 6.04 | <1 | 0.5 | — | 1 | — |

TABLE 2

Biological Activity of N-5 Oxygen-Containing Derivatives.

| Cp. # | R' | R | X | GABA$_A$ Receptor Binding IC$_{50}$ (nM) | Mouse Metrazol (ED$_{50}$, mg/kg) ip | Mouse Metrazol (ED$_{50}$, mg/kg) po | Rat Conflict (MED, mg/kg) ip | Rat Conflict (MED, mg/kg) po | Squirrel Monkey Conflict (mg/kg, po) |
|---|---|---|---|---|---|---|---|---|---|
| 91 | 2-FPh | —(CH$_2$)$_2$—C(OCH$_2$)$_2$CHMe (4-Me-2,6,7-trioxabicyclo) | 7-F | 6.21 | 1 | 30 | — | >10 | — |
| 92 | 2-F-4-(PhCH$_2$O)Ph | —CH$_2$OEt | 7-F | 3.33 | — | — | — | >3 | — |
| 93 | 2-F-4-(MeOCH$_2$CH$_2$O)Ph | —CH$_2$OEt | 7-F | 1.80 | — | — | — | ≦0.3 | — |
| 94 | 2-FPh | —CH$_2$CH$_2$OH | 6-OH | 2.38 | — | — | — | >10 | — |
| 95 | 2-F-4-(iPrO)Ph | —CH$_2$OEt | 7-F | 2.50 | — | — | — | ≦3 | — |
| 96 | 2-FPh | —CH$_2$CH$_2$OMe | 6-MeO | 1.80 | — | — | — | >10 | — |
| 97 | 2-F-4-(MeO)Ph | —CH$_2$OEt | 7-F | 0.41 | — | ≦0.3 | ≦0.1 | 0.03 | ≦1 |
| 98 | 2-[(5-Me)thiazoyl] | —CH$_2$CH$_2$OMe | H | 11.0 | — | — | — | 3 | — |
| 99 | 2-F-4-(OH)Ph | —CH$_2$OEt | 7-F | 1.38 | — | 0.3–3 | ≦1 | 1–3 | 20 |
| 100 | 2-F-4-[MeOC(O)O]Ph | —CH$_2$OEt | 7-F | 4.35 | ≧1 | 3–30 | — | ca. 1 | — |
| 101 | 2-[(5-Me)thienyl] | —CH$_2$OEt | H | 0.95 | <1 | <3 | — | 3 | — |
| 102 | 2-thiazolyl | —CH$_2$CH$_2$OMe | H | 8.82 | ca. 1 | ca. 6 | — | 10 | — |
| 103 | 2-FPh | —CH$_2$OEt | 6,7-F$_2$ | 0.55 | <1 | <3 | — | 1 | — |
| 104 | 4-(MeO)Ph | —CH$_2$OEt | 7-F | 1.04 | <1 | <3 | — | 0.1 | ≦3 |
| 105 | 2-thienyl | —CH$_2$OEt | H | 0.84 | <1 | <3 | — | 10 | — |
| 106 | 4-(MeO)Ph | —CH$_2$CH$_2$OMe | 7-F | 4.47 | <1 | 0.3 | — | 1 | — |
| 107 | -cyclohexyl | —CH$_2$CH$_2$OMe | 7-F | 8.01 | <1 | 10 | — | 10 | — |
| 108 | 2-FPh | —CH$_2$CH$_2$OMe | 9-OH | 10.4 | >1 | ≧30 | — | >10 | — |
| 109 | 2-FPh | —CH$_2$CH$_2$OMe | 9-PhCH$_2$O | >1000 | — | — | — | >10 | — |
| 110 | -cyclohexyl | —CH$_2$CH$_2$OMe | 7-F | 19.1 | ≧1 | ≧30 | — | 10 | — |
| 111 | -cyclopropyl | —CH$_2$OEt | 7-F | 1.90 | >1 | >30 | — | >10 | — |
| 112 | 2-FPh | —CH$_2$OEt | 6,8-F$_2$ | 13.3 | — | — | — | >10 | — |
| 113 | 2,4-F$_2$Ph | —CH$_2$OEt | 6,8-F$_2$ | 44.3 | — | — | — | >10 | — |
| 114 | 2-FPh | —(CH$_2$)$_2$OC(O)OMe | 7-F | 0.3 | <1 | ≦3 | — | 3 | — |
| 115 | 2-benzothienyl | —CH$_2$OEt | 7-F | 53.5 | >1 | >30 | — | — | — |
| 116 | 2-benzothienyl | —CH$_2$OEt | H | 100 | >1 | >30 | — | >10 | — |
| 117 | 2-benzothienyl | —CH$_2$CH$_2$OEt | 7-F | 106 | ≦1 | >30 | — | — | — |
| 118 | -cyclopropyl | —CH$_2$CH$_2$OMe | 7-F | 3.68 | <1 | ca. 3 | — | 10 | — |
| 119 | 2-FPh | —CH$_2$CH$_2$OAc | 7-F | 0.25 | <1 | ≦3 | — | 3 | — |
| 120 | 2-[(5-SO$_2$Me)thienyl] | —CH$_2$OEt | 7-F | 35.1 | <1 | ca. 3 | — | >10 | — |
| 121 | 2-[(5-SO$_2$Me)thienyl] | —CH$_2$CH$_2$OEt | 7-F | 84.0 | >1 | >30 | — | >10 | — |
| 122 | 2-[(5-Cl)thienyl] | —CH$_2$OEt | 7-F | 3.64 | ≦1 | ≦3 | — | ca. 3 | — |
| 123 | 2,4-F$_2$Ph | —CH$_2$OEt | 7-F | 1.19 | <1 | <3 | ≦0.1 | 0.1 | 1 |
| 124 | 3-thienyl | —CH$_2$OEt | 7-F | 0.98 | <1 | ca. 0.2 | — | ca. 0.3 | — |
| 125 | 2-[(3-Cl)thienyl] | —CH$_2$CH$_2$OEt | 7-F | 0.89 | <1 | >30 | — | >10 | — |
| 126 | 2-thienyl | —CH$_2$CH$_2$OEt | 7-F | 0.73 | <1 | ca. 0.6 | — | 0.1 | ≦3 |
| 127 | 2,6-F$_2$Ph | —CH$_2$OEt | 8,9-F$_2$ | 585 | ca. 1 | >30 | — | >10 | — |
| 128 | 2-FPh | —CH$_2$OEt | 8,9-F$_2$ | 126 | ≧1 | >30 | — | >10 | — |
| 128 | 2-[(3-Cl)thienyl] | —CH$_2$OEt | 7-F | 0.66 | <1 | ca. 10 | — | >10 | — |
| 129 | 2-thienyl | —CH$_2$OEt | 7-F | 1.05 | <1 | ca. 0.2 | — | 3 | >10 |
| 130 | 4-[(2-F)pyridyl] | —CH$_2$CH$_2$OEt | 7-F | 2.27 | <1 | ca. 0.8 | — | 1 | — |
| 131 | 2-[(5-Me)thienyl] | —CH$_2$CH$_2$OEt | 7-F | 1.03 | <1 | ca. 0.6 | — | ca. 1 | — |
| 132 | 2-[(5-Cl)thienyl] | —CH$_2$CH$_2$OEt | 7-F | 3.13 | — | — | — | >3 | — |
| 133 | 2-[(5-Me)thienyl] | —CH$_2$OEt | 7-F | 0.68 | — | — | — | >3 | — |
| 134 | 2-[(5-Cl)thienyl] | —CH$_2$OEt | 7-F | 1.81 | <1 | 2 | — | >10 | — |
| 135 | 2-[(5-Br)thienyl] | —CH$_2$CH$_2$OMe | 7-F | 1.50 | <1 | ca. 10 | — | ca. 10 | — |
| 136 | 2,4-F$_2$Ph | —CH$_2$CH$_2$OMe | 7-F | 5.55 | <1 | 0.3 | — | 0.3 | >3 |
| 137 | 2,4-F$_2$Ph | —CH$_2$CH$_2$OEt | 7-F | 2.40 | <1 | 0.15 | 1 | 1 | — |
| 138 | 2-[(3-Cl)thienyl] | —CH$_2$CH$_2$OMe | 7-F | 1.34 | <1 | 30 | — | >10 | — |
| 139 | 2-thienyl | —CH$_2$CH$_2$OMe | 7-F | 1.79 | <1 | ca. 0.2 | — | ca. 1 | — |
| 140 | 2-thiazolyl | —CH$_2$CH$_2$OMe | 7-F | 3.97 | <1 | 0.3 | — | >10 | — |
| 141 | 2-thiazolyl | —CH$_2$CH$_2$OEt | 7-F | 6.78 | <1 | ca. 6 | — | >3 | — |
| 142 | 2-[(5-Me)thienyl] | —CH$_2$CH$_2$OMe | H | 3.17 | <1 | 0.7 | — | ca. 1 | — |
| 143 | 2-[(5-Me)thienyl] | —CH$_2$CH$_2$OMe | 7-F | 1.35 | <1 | 0.7 | — | <10 | — |

TABLE 2-continued

Biological Activity of N-5 Oxygen-Containing Derivatives.

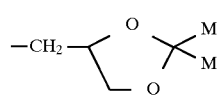

| Cp. # | R' | R | X | GABA$_A$ Receptor Binding IC$_{50}$ (nM) | Mouse Metrazol (ED$_{50}$, mg/kg) ip | Mouse Metrazol (ED$_{50}$, mg/kg) po | Rat Conflict (MED, mg/kg) ip | Rat Conflict (MED, mg/kg) po | Squirrel Monkey Conflict (mg/kg, po) |
|---|---|---|---|---|---|---|---|---|---|
| 144 | 2-[(5-Br)thienyl] | —CH$_2$CH$_2$OMe | 7-F | 5.26 | <1 | ca. 10 | — | >10 | — |
| 145 | 2-[(5-Cl)thienyl] | —CH$_2$CH$_2$OMe | 7-F | 2.05 | <1 | ca. 30 | — | >10 | — |
| 146 | 2-[(5-Cl)thienyl] | —CH$_2$CH$_2$OMe | H | 2.09 | <1 | >30 | — | >10 | — |
| 147 | 2-FPh | —CH$_2$CH$_2$OMe | 7-Cl | 2.49 | <1 | ca. 5 | — | >10 | — |
| 148 | 2-FPh | —CH$_2$CH$_2$OMe | 7-CF$_3$ | 1.98 | <1 | ca. 10 | — | >10 | — |
| 149 | 2-FPh | —CH$_2$CH$_2$OMe | 6,7-F$_2$ | 1.08 | <1 | 3 | — | >10 | — |
| 150 | 2-FPh | —CH$_2$CH$_2$OiPr | 7-F | 0.32 | <1 | 1 | — | 10 | — |
| 151 | 2,6-F$_2$Ph | —CH$_2$CH$_2$OMe | H | 4.64 | <1 | ca. 2 | — | 10 | — |
| 152 | 2-FPh | —CH$_2$CH$_2$CH$_2$OEt | 7-F | 0.28 | <1 | ca. 0.3 | — | 1 | — |
| 153 | 2-FPh | —CH$_2$CH$_2$OMe | H | 1.3 | <1 | 1 | — | ≦1 | — |
| 154 | 2-FPh | —(CH$_2$)$_2$CH(OEt)$_2$ | 7-F | 6.98 | <1 | ca. 3 | — | 3 | — |
| 155 | 2-thiazolyl | —CH$_2$CH$_2$OMe | 7-F | 6.13 | <1 | ca. 1.5 | — | 3 | 10 |
| 156 | 4-ClPh | —CH$_2$CH$_2$OMe | H | 16.0 | <1 | ca. 2 | — | 1 | — |
| 157 | 2-FPh | —CH$_2$OEt | 7-Cl | 0.48 | <1 | ca. 2 | — | >10 | — |
| 158 | 2-FPh | —CH$_2$OMe | 7-F | 0.15 | 0.01 | 0.1 | <10 | 3 | — |
| 159 | 2-FPh | —CH$_2$O(CH$_2$)$_2$OMe | 7-F | 0.80 | 0.003 | 0.1 | <<10 | 3 | — |
| 160 | 2-FPh | —CH$_2$CH$_2$OEt | 7-F | 0.48 | <1 | 0.3 | <10 | 1 | — |
| 162 | 2-FPh | —CH$_2$CH(OH)CH$_2$OH | 7-F | 16.0 | 3 | ≦30 | ≦10 | >10 | — |
| 163 | 2-FPh | —CH$_2$CH$_2$OMe | 7-F | 0.61 | 0.01 | 0.2 | <10 | 0.1 | — |
| 164 | 2-FPh | 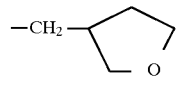 | 7-F | 2.75 | 0.1 | 1 | <10 | 10 | — |
| 165 | 3 pyridyl | —CH$_2$CH$_2$OCH$_2$Ph | 7-F | 39.2 | 3 | >30 | >7 | — | — |
| 166 | 2-FPh | —(CH$_2$)$_2$O(CH$_2$)$_2$OMe | 7-F | 1.93 | 0.01 | ca. 0.1 | <10 | 10 | — |
| 167 | 2-FPh | —CH$_2$OCH$_2$Ph | 7-F | 0.26 | <1 | <30 | >10 | >10 | — |
| 168 | 2-FPh | —CH$_2$CH$_2$OH | 7-F | 1.17 | <1 | <30 | 10 | >10 | — |
| 169 | 2-FPh | —CH$_2$CH$_2$CH$_2$OH | 7-F | 1.08 | 0.1 | 0.5 | 10 | 10 | — |
| 170 | 2-FPh | —(CH$_2$)$_3$OCH$_2$Ph | 7-F | 0.21 | <1 | <30 | <10 | >10 | — |
| 171 | 2-FPh | —CH$_2$CH$_2$OCH$_2$Ph | 7-F | 1.50 | 0.1 | 1 | 10 | 10 | — |
| 172 | 2-FPh | —CH$_2$OEt | 7-F | 0.14 | 0.01 | 0.1 | ≦10 | 0.3 | 1 |
| 173 | 2,6-F$_2$Ph | —CH$_2$OEt | 7-F | 0.65 | 1 | 3 | >10 | >10 | >10 |
| 174 | 2-FPh | 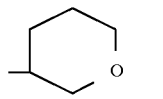 | 7-F | 2.28 | <1 | <3 | — | 3 | — |
| 175 | 2-FPh | | 7-F | 1.50 | <1 | 2 | — | >10 | — |
| 176 | 2-FPh | —CH$_2$C(O)OtBu | 7-F | 56.2 | >1 | >30 | — | >10 | — |
| 177 | 2-FPh | —CH$_2$CO$_2$H | 7-F | 54.8 | >1 | >30 | — | >10 | — |
| 178 | 2-Fph | | 7-F | 2.29 | <1 | >30 | — | >10 | — |
| 179 | 2,6-F$_2$Ph | —CH$_2$CH$_2$OC(O)NH(2,6-F$_2$Ph) | 7-F | 7.65 | 10 | >30 | >10 | — | — |

TABLE 2-continued

Biological Activity of N-5 Oxygen-Containing Derivatives.

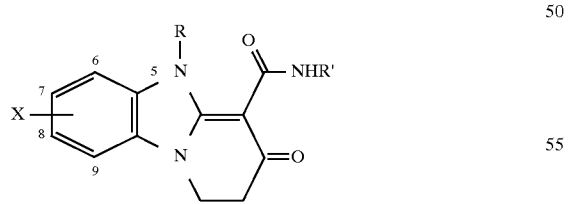

| Cp. # | R' | R | X | GABA$_A$ Receptor Binding IC$_{50}$ (nM) | Mouse Metrazol (ED$_{50}$, mg/kg) ip | Mouse Metrazol (ED$_{50}$, mg/kg) po | Rat Conflict (MED, mg/kg) ip | Rat Conflict (MED, mg/kg) po | Squirrel Monkey Conflict (mg/kg, po) |
|---|---|---|---|---|---|---|---|---|---|
| 180 | 2-FPh | −CH$_2$−(oxetanyl, Me) | 7-F | 18.0 | 1 | >30 | — | >10 | — |
| 181 | 2-FPh | −CH$_2$CH$_2$CO$_2$Me | 7-F | 0.67 | >1 | >30 | — | >10 | — |

TABLE 3

Biological Activity of N-5 Sulfur-Containing Derivatives.

| Cp. # | R' | R | X | GABA$_A$ Receptor Binding IC$_{50}$ (nM) | Mouse Metrazol (ED$_{50}$, mg/kg) ip | Mouse Metrazol (ED$_{50}$, mg/kg) po | Rat Conflict (MED, mg/kg) ip | Rat Conflict (MED, mg/kg) po | Squirrel Monkey Conflict (mg/kg, po) |
|---|---|---|---|---|---|---|---|---|---|
| 181 | 2-FPh | −CH$_2$CH$_2$SMe | 7-F | 1.82 | <1 | ca. 10 | — | >10 | — |
| 183 | 2-FPh | −CH$_2$CH$_2$S(O)Me | 7-F | 6.19 | >1 | ca. 10 | — | 10 | — |

We claim:

1. A compound represented by the following formula 1:

wherein X is independently selected from hydrogen, alkyl(C$_1$–C$_8$), halogen, perfluoro(lower alkyl), hydroxy, C$_1$–C$_4$ alkoxy, di(C$_1$–C$_4$ alkyl)amino, C$_1$–C$_4$ alkoxycarbonyl or C$_1$–C$_4$ alkylthio;

wherein R is selected from
(CH$_2$)$_n$NR$_2$R$_3$, where n=1–4, R$_2$ and R$_3$ may be the same or different and are selected from hydrogen, alkyl(C$_1$–C$_{12}$), perfluoro(C$_1$–C$_4$ alkyl), cycloalkyl (C$_3$–C$_{10}$), alkoxy(C$_1$–C$_8$), phenyl or substituted phenyl, where the phenyl substituents are selected from alkyl(C$_1$–C$_8$), branched alkyl(C$_3$–C$_8$), halogen, perfluoro(C$_1$–C$_4$ alkyl), hydroxy, C$_1$–C$_4$ alkoxy, di(C$_1$–C$_4$ alkyl)amino, C$_1$–C$_4$ alkoxycarbonyl or C$_1$–C$_4$ alkylthio; or R$_2$ and R$_3$ may be taken together with the nitrogen to form a cycloalkylamine(C$_3$–C$_{10}$), substituted piperazine, substituted morpholine, amidine, substituted amidine or guanidine wherein the substituted piperazine, morpholine and amidine may be substituted with up to three substituents independently selected from C$_1$–C$_4$ alkyl or aralkyl (C$_1$–C$_4$); or (CH$_2$)$_n$N(R$_4$)C(O)R$_5$, where n=1–4, R$_4$ is selected from hydrogen, alkyl(C$_1$–C$_{12}$) or cycloalkyl(C$_3$–C$_{10}$), R$_5$ is selected from alkyl(C$_1$–C$_{12}$), perfluoro(C$_1$–C$_4$ alkyl), cycloalkyl(C$_3$–C$_{10}$), alkoxy(C$_1$–C$_8$), phenyl or substituted phenyl, where the phenyl substituents are selected from alkyl(C$_1$–C$_8$), branched alkyl (C$_3$–C$_8$), halogen, perfluoro(C$_1$–C$_4$ alkyl), hydroxy, C$_1$–C$_4$ alkoxy, di(C$_1$–C$_4$ alkyl)amino, C$_1$–C$_4$ alkoxycarbonyl or C$_1$–C$_4$ alkylthio; or R$_5$ is a heteroaryl selected from pyridine, pyridine-N-oxide, thiazole, thiophene, indole, benzothiophene, pyridazine, pyrimidine, indole, benzofuran, isoquinoline, or oxazole which heterocycle may be substituted with one or more substituents which are independently selected from halogen, nitro, lower amido, lower alkoxy, di(lower alkyl)amino, carboxy, lower alkoxycarbonyl, or lower alkyl; or $N(R_4)C(O)R_5$ may be a substituted carbamate or urea wherein the substituents are selected from alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; or $(CH_2)_nN(R_4)S(O)_2R_6$, where n=1–4, $R_4$ is previously defined, $R_6$ is selected from alkyl($C_1$–$C_{12}$), perfluoro ($C_1$–$C_4$ alkyl), cycloalkyl($C_3$–$C_{10}$), alkoxy($C_1$–$C_8$), phenyl and substituted phenyl, where the phenyl substituents are selected from alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; or $R_6$ may also be a heterocycle selected from pyridine, pyridine-N-oxide, thiazole, thiophene, indole, benzothiophene, pyridazine, pyrimidine, indole, benzofuran, isoquinoline, or oxazole, which heterocycle may be substituted with one or more substituents which are independently selected from halogen, nitro, $C_1$–$C_4$ amido, $C_1$–$C_4$ alkoxy, di($C_1$–$C_4$ alkyl) amino, carboxy, $C_1$–$C_4$ alkoxycarbonyl, or $C_1$–$C_4$ alkyl; or $(CH_2)nOR_7$, where n=1–4, $R_7$ is selected from hydrogen, alkyl($C_1$–$C_{12}$), cycloalkyl($C_3$–$C_{10}$), phenyl or substituted phenyl, where the phenyl substituents are selected from alkyl($C_1$–$C_8$), branched alkyl ($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or $(CH_2)_nCR_8R_9OR_{10}$, where n=1–3 and $R_8$ and $R_9$ are either one or both $OR_{11}$; if both $R_8$ or $R_9$ are not $OR_{11}$, then the non-$OR_{11}$ substituent is either H or lower alkyl, $R_{10}$ and $R_{11}$ are lower alkyl and are the same or different and taken together to form a ring of 4–7 members; or $(CH_2)_nCN$, where n=1–3; or $(CH_2)_nS(O)_mR_7$, where n=1–4 and m=0–2, $R_7$ is selected from hydrogen, alkyl($C_1$–$C_{12}$), cycloalkyl ($C_3$–$C_{10}$), phenyl or substituted phenyl, where the phenyl substituents are selected from alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; or $(CH_2)nC(O)NR_4R_{12}$, where n=1–3, $R_4$ is as previously defined, and $R_{12}$ is defined as $R_4$ except that $R_4$ and $R_{12}$ do not need to be the same in any particular compound; or $(CH_2)_nC(O)OR_{13}$ where n=1–4 and $R_{13}$ is hydrogen or lower alkyl($C_1$–$C_6$);

wherein R' is selected from phenyl, substituted phenyl, where the phenyl substituents are selected from alkyl ($C_1$–$C_8$), branched alkyl($C_3$–$C_8$), halogens, perfluoro ($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; a heterocycle selected from pyridine, pyridine-N-oxide, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole, which heterocycle may be substituted with one or more substituents which are independently selected from halogen, perfluoro ($C_1$–$C_4$)alkyl, nitro, $C_1$–$C_4$ alkylthio, $C_1$–$C_4$ alkoxy, $C_1$–$C_4$ alkyl, di($C_1$–$C_4$ alkyl)amino, carboxy, $C_1$–$C_4$ alkoxycarbonyl; or a cycloalkyl ring comprising 3–8 carbon atoms;

or a pharmaceutically acceptable salt, solvate or hydrate thereof.

2. The compound of claim 1, wherein X is selected from lower alkoxy, hydrogen, halogen, or alkyl($C_1$–$C_8$).

3. The compound of claim 2, wherein there is only one X substituent other than hydrogen.

4. The compound of claim 3, wherein X is 7-F.

5. The compound of claim 1, wherein R is $(CH_2)nOR_7$, where n=1–4, $R_7$ is selected from hydrogen, alkyl($C_1$–$C_{12}$), cycloalkyl($C_3$–$C_{10}$, phenyl or substituted phenyl, where the phenyl substituents are selected from alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio.

6. The compound of claim 5, wherein R is 2-methoxyethyl, 2-ethoxyethyl, methoxymethyl, or ethoxymethyl.

7. The compound of claim 4, wherein R is 2-methoxyethyl, 2-ethoxyethyl, methoxymethyl, or ethoxymethyl.

8. The compound of claim 1, wherein R' is substituted phenyl.

9. The compound of claim 1, wherein R' is 2,4-diFPh or 2-FPh or 2-F-4-(HO)Ph.

10. The compound of claim 4, wherein R' is 2,4-diFPh or 2-FPh or 2-F-4-(HO)Ph.

11. The compound of claim 7, wherein R' is 2,4-diFPh or 2-FPh or 2-F-4-(HO)Ph.

12. The compound of claim 1, selected from

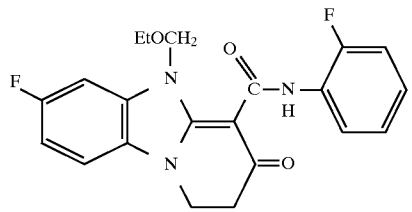

5-Ethoxymethyl-7-fluoro-4-
[N-(2-fluorophenyl)carboxamido]-
1,2-dihydro-3-oxopyrido[1,2-a]
benzimidazole, -continued

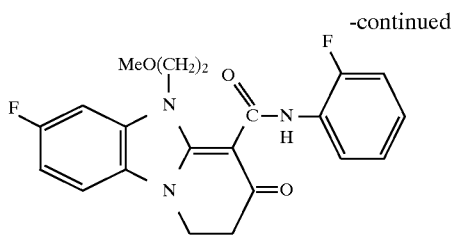

5-Methoxyethyl-7-fluoro-4-
[N-(2-fluorophenyl)carboxamido]-
1,2-dihydro-3-oxopyrido[1,2-a]
benzimidazole,

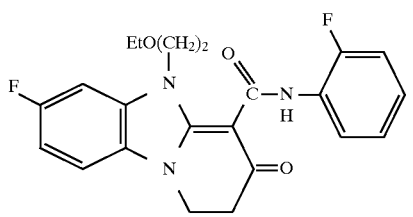

5-Ethoxyethyl-7-fluoro-4-
[N-(2-fluorophenyl)carboxamido]-
1,2-dihydro-3-oxopyrido[1,2-a]
benzimidazole,

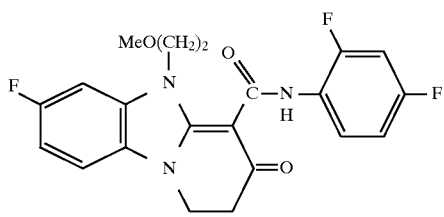

5-Methoxyethyl-7-fluoro-4-
[N-(2,4-difluorophenyl)carboxamido]-
1,2-dihydro-3-oxopyrido[1,2-a]
benzimidazole,

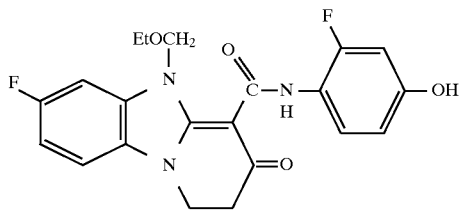

5-Ethoxyethyl-7-fluoro-4-
[N-(2-fluoro-4-hydroxyphenyl)-
carboxamido]-1,2-dihydro-3-
oxopyrido[1,2-a]benzimidazole, or a pharmaceutically acceptable salt, solvate or hydrate thereof.

13. The compound of claim 12, which is

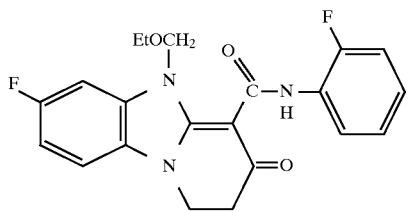

5-Ethoxymethyl-7-fluoro-4-
[N-(2-fluorophenyl)carboxamido]-
1,2-dihydro-3-oxopyrido[1,2-a]
benzimidazole or its pharmaceutically acceptable salt, solvate or hydrate thereof.

14. A pharmaceutical composition comprising a compound of formula 1:

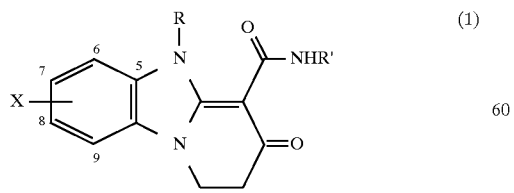

(1)

wherein X is independently selected from hydrogen, alkyl($C_1$–$C_8$), halogen, perfluoro(lower alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio;

wherein R is selected from
($CH_2$)$_n$$NR_2R_3$, where n=1–4, $R_2$ and $R_3$ may be the same or different and are selected from hydrogen, alkyl($C_1$–$C_{12}$), perfluoro($C_1$–$C_4$ alkyl), cycloalkyl ($C_3$–$C_{10}$), alkoxy($C_1$–$C_8$), phenyl or substituted phenyl, where the phenyl substituents are selected from alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or $R_2$ and $R_3$ may be taken together with the nitrogen to form a cycloalkylamine ($C_3$–$C_{10}$), substituted piperazine, substituted morpholine, amidine, substituted amidine or guanidine wherein the substituted piperazine, morpholine and amidine may be substituted with up to three substituents independently selected from $C_1$–$C_4$ alkyl or aralkyl($C_1$–$C_4$); or ($CH_2$)$_n$$N(R_4)C(O)R_5$, where n=1–4, $R_4$ is selected from hydrogen, alkyl($C_1$–$C_{12}$) or cycloalkyl($C_3$–$C_{10}$), $R_5$ is selected from alkyl($C_1$–$C_{12}$), perfluoro($C_1$–$C_4$ alkyl), cycloalkyl($C_3$–$C_{10}$), alkoxy($C_1$–$C_8$), phenyl or substituted phenyl, where the phenyl substituents are selected from alkyl($C_1$–$C_8$), branched alkyl ($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or $R_5$ is a heteroaryl selected from pyridine, pyridine-N-oxide, thiazole, thiophene, indole, benzothiophene, pyridazine, pyrimidine, indole, benzofuran, isoquinoline, or oxazole which heterocycle may be substituted with one or more substituents which are independently selected from halogen, nitro, lower amido, lower alkoxy, di(lower alkyl)amino, carboxy, lower alkoxycarbonyl, or lower alkyl; or N($R_4$)C(O)$R_5$ may be a substituted carbamate or urea wherein the substituents are selected from alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; or $(CH_2)_nN(R_4)S(O)_2R_6$, where n=1–4, $R_4$ is previously defined, $R_6$ is selected from alkyl($C_1$–$C_{12}$), perfluoro ($C_1$–$C_4$ alkyl), cycloalkyl($C_3$–$C_{10}$), alkoxy($C_1$–$C_8$), phenyl and substituted phenyl, where the phenyl substituents are selected from alkyl($C_{1-C8}$), branched alkyl($C_3$–$C_8$), halogen, perfluoro($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; or $R_6$ may also be a heterocycle selected from pyridine, pyridine-N-oxide, thiazole, thiophene, indole, benzothiophene, pyridazine, pyrimidine, indole, benzofuran, isoquinoline, or oxazole, which heterocycle may be substituted with one or more substituents which are independently selected from halogen, nitro, $C_1$–$C_4$ amido, $C_1$–$C_4$ alkoxy, di($C_1$–$C_4$alkyl) amino, carboxy, $C_1$–$C_4$alkoxycarbonyl, or $C_1$–$C_4$ alkyl; or $(CH_2)nOR_7$, where n=1–4, $R_7$ is selected from hydrogen, alkyl($C_1$–$C_{12}$), cycloalkyl($C_3$–$C_{10}$), phenyl or substituted phenyl, where the phenyl substituents are selected from alkyl($C_1$–$C_8$), branched alkyl ($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or $(CH_2)_nCR_8R_9OR_{10}$, where n=1–3 and $R_8$ and $R_9$ are either one or both $OR_{11}$; if both $R_8$ or $R_9$ are not $OR_{11}$, then the non-$OR_{11}$ substituent is either H or lower alkyl, $R_{10}$ and $R_{11}$ are lower alkyl and are the same or different and taken together to form a ring of 4–7 members; or $(CH_2)_nCN$, where n=1–3; or $(CH_2)_nS(O)_mR_7$, where n=1–4 and m=0–2, $R_7$ is selected from hydrogen, alkyl($C_1$–$C_{12}$), cycloalkyl ($C_3$–$C_{10}$), phenyl or substituted phenyl, where the phenyl substituents are selected from alkyl($C_1$–$C_8$), branched alkyl($C_3$–$C_8$), halogen, perfluoro($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; or $(CH_2)nC(O)NR_4R_{12}$, where n=1–3, $R_4$ is as previously defined, and $R_{12}$ is defined as $R_4$ except that $R_4$ and $R_{12}$ do not need to be the same in any particular compound; or $(CH_2)_nC(O)OR_{13}$ where n=1–4 and $R_{13}$ is hydrogen or lower alkyl($C_1$–$C_6$);

wherein R' is selected from phenyl, substituted phenyl, where the phenyl substituents are selected from alkyl ($C_1$–$C_8$), branched alkyl($C_3$–$C_8$), halogens, perfluoro ($C_1$–$C_4$ alkyl), hydroxy, $C_1$–$C_4$ alkoxy, di($C_1$–$C_4$ alkyl) amino, $C_1$–$C_4$ alkoxycarbonyl or $C_1$–$C_4$ alkylthio; a heterocycle selected from pyridine, pyridine-N-oxide, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole, which heterocycle may be substituted with one or more substituents which are independently selected from halogen, perfluoro ($C_1$–$C_4$)alkyl, nitro, $C_1$–$C_4$ alkylthio, $C_1$–$C_4$ alkoxy, $C_1$–$C_4$ alkyl, di($C_1$–$C_4$ alkyl)amino, carboxy, $C_1$–$C_4$ alkoxycarbonyl; or a cycloalkyl ring comprising 3–8 carbon atoms;

or a pharmaceutically acceptable salt, solvate or hydrate thereof in an amount effective for treating disorders of the central nervous system and a pharmaceutically acceptable carrier or diluent.

15. A method for treating disorders of the central nervous system comprising administering a compound of the formula 1:

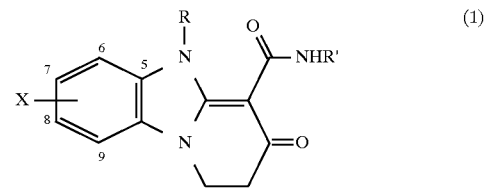

wherein X is independently selected from hydrogen, alkyl($C_{1-C8}$), halogen, perfluoro(lower alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio;

wherein R is selected from $(CH_2)_nNR_2R_3$, where n=1–4, $R_2$ and $R_3$ may be the same or different and are selected from hydrogen, alkyl($C_1$–$C_{12}$), perfluoro($C_1$–$C_4$ alkyl), cycloalkyl ($C_{3-C10}$), alkoxy($C_1$–$C_8$), phenyl or substituted phenyl, where the phenyl substituents are selected from alkyl($C_{1-C8}$), branched alkyl($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or $R_2$ and $R_3$ may be taken together with the nitrogen to form a cycloalkylamine ($C_3$–$C_{10}$), substituted piperazine, substituted morpholine, amidine, substituted amidine or guanidine wherein the substituted piperazine, morpholine and amidine may be substituted with up to three substituents independently selected from $C_1$–$C_4$ alkyl or aralkyl($C_1$–$C_4$); or $(CH_2)_nN(R_4)C(O)R_5$, where n=1–4, $R_4$ is selected from hydrogen, alkyl($C_1$–$C_{12}$) or cycloalkyl($C_3$–$C_{10}$), $R_5$ is selected from alkyl($C_1$–$C_{12}$), perfluoro($C_1$–$C_4$ alkyl), cycloalkyl($C_3$–$C_{10}$), alkoxy($C_1$–$C_8$), phenyl or substituted phenyl, where the phenyl substituents are selected from alkyl($C_{l\ -C8}$), branched alkyl ($C_3$–$C_8$), halogen, perfluoro($C_1$–$C_4$ alkyl), hydroxy, $C_1$–$C_4$ alkoxy, di($C_1$–$C_4$ alkyl)amino, $C_1$–$C_4$ alkoxycarbonyl or $C_1$–$C_4$ alkylthio; or $R_5$ is a heteroaryl selected from pyridine, pyridine-N-oxide, thiazole, thiophene, indole, benzothiophene, pyridazine, pyrimidine, indole, benzofuran, isoquinoline, or oxazole which heterocycle may be substituted with one or more substituents which are independently selected from halogen, nitro, lower amido, lower alkoxy, di(lower alkyl)amino, carboxy, lower alkoxycarbonyl, or lower alkyl; or N($R_4$)C(O)$R_5$ may be a substituted carbamate or urea wherein the substituents are selected from alkyl($C_1-C_8$), branched alkyl($C_3-C_8$), halogen, perfluoro($C_1-C_4$ alkyl), hydroxy, $C_1-C_4$ alkoxy, di($C_1-C_4$ alkyl)amino, $C_1-C_4$ alkoxycarbonyl or $C_1-C_4$ alkylthio; or $(CH_2)_nN(R_4)S(O)_2R_6$, where n=1–4, $R_4$ is previously defined, $R_6$ is selected from alkyl($C_1-C_{12}$), perfluoro($C_1-C_4$ alkyl), cycloalkyl($C_3-C_{10}$), alkoxy($C_1-C_8$), phenyl and substituted phenyl, where the phenyl substituents are selected from alkyl($C_1-C_8$), branched alkyl($C_3-C_8$), halogen, perfluoro($C_1-C_4$ alkyl), hydroxy, $C_1-C_4$ alkoxy, di($C_1-C_4$ alkyl)amino, $C_1-C_4$ alkoxycarbonyl or $C_1-C_4$ alkylthio; or $R_6$ may also be a heterocycle selected from pyridine, pyridine-N-oxide, thiazole, thiophene, indole, benzothiophene, pyridazine, pyrimidine, indole, benzofuran, isoquinoline, or oxazole, which heterocycle may be substituted with one or more substituents which are independently selected from halogen, nitro, $C_1-C_4$ amido, $C_1-C_4$ alkoxy, di($C_1-C_4$ alkyl)amino, carboxy, $C_1-C_4$ alkoxycarbonyl, or $C_1-C_4$ alkyl; or $(CH_2)nOR_7$, where n=1–4, is selected from hydrogen, alkyl($C_1-C_{12}$), cycloalkyl($C_3-C_{10}$), phenyl or substituted phenyl, where the phenyl substituents are selected from alkyl($C_1-C_8$), branched alkyl($C_3-C_8$), halogen, perfluoro($C_1-C_4$alkyl), hydroxy, $C_1-C_4$ alkoxy, di($C_1-C_4$ alkyl)amino, $C_1-C_4$ alkoxycarbonyl or $C_1-C_4$ alkylthio; or $(CH_2)_nCR_8R_9OR_{10}$, where n=1–3 and $R_8$ and $R_9$ are either one or both $OR_{11}$; if both $R_8$ or $R_9$ are not $OR_{11}$, then the non-$OR_{11}$ substituent is either H or lower alkyl, $R_{10}$ and $R_{11}$ are lower alkyl and are the same or different and taken together to form a ring of 4–7 members; or $(CH_2)_nCN$, where n=1–3; or $(CH_2)_nS(O)_mR_7$, where n=1–4 and m=0–2, $R_7$ is selected from hydrogen, alkyl($C_1-C_{12}$), cycloalkyl($C_3-C_{10}$), phenyl or substituted phenyl, where the phenyl substituents are selected from alkyl($C_1-C_8$), branched alkyl($C_3-C_8$), halogen, perfluoro($C_1-C_4$ alkyl), hydroxy, $C_1-C_4$ alkoxy, di($C_1-C_4$ alkyl)amino, $C_1-C_4$ alkoxycarbonyl or $C_1-C_4$ alkylthio; or $(CH_2)nC(O)NR_4R_{12}$, where n=1–3, $R_4$ is as previously defined, and $R_{12}$ is defined as $R_4$ except that $R_4$ and $R_{12}$ do not need to be the same in any particular compound; or $(CH_2)_nC(O)OR_{13}$ where n=1–4 and $R_{13}$ is hydrogen or lower alkyl($C_1-C_6$);

wherein R' is selected phenyl, substituted phenyl, where the phenyl substituents are selected from alkyl($C_1-C_8$), branched alkyl($C_3-C_8$), halogens, perfluoro($C_1-C_4$ alkyl), hydroxy, $C_1-C_4$ alkoxy, di($C_1-C_4$ alkyl)amino, $C_1-C_4$ alkoxycarbonyl or $C_1-C_4$ alkylthio; a heterocycle selected from pyridine, pyridine-N-oxide, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole, which heterocycle may be substituted with one or more substituents which are independently selected from halogen, perfluoro($C_1-C_4$)alkyl, nitro, $C_1-C_4$ alkylthio, $C_1-C_4$ alkoxy, $C_1-C_4$ alkyl, di($C_1-C_4$ alkyl)amino, carboxy, $C_1-C_4$ alkoxycarbonyl; or a cycloalkyl ring comprising 3–8 carbon atoms;

or a pharmaceutically acceptable salt, solvate, or hydrate thereof, to a mammal affiliated with a disorder of the central nervous system in an amount effective for treating such disorder.

16. The method of claim 15, wherein the effective amount is of from about 0.2 to 25 mg/kg per day.

17. The method of claim 15, wherein the disorder is anxiety.

18. The method of claim 15 wherein the disorder is convulsions.

19. The method of claim 15 wherein the disorder is sleeplessness.

20. The method of claim 15 wherein the disorder is muscle spasm.

21. The method of claim 15 wherein the disorder is benzodiazepine drug overdose.

* * * * *

UNITED STATES PATENT AND TRADEMARK OFFICE
CERTIFICATE OF CORRECTION

PATENT NO. : 5,817,660
DATED : October 6, 1998
INVENTOR(S) : Allen B. Reitz et al.

It is certified that error appears in the above-indentified patent and that said Letters Patent is hereby corrected as shown below:

Column 42, Line 53, delete "($C_3$-$C_{10}$)" and insert -- ($C_3$-$C_{10}$) --

Column 44, Line 33, delete "($C_3$-$C_{10}$," and insert -- ($C_3$-$C_{10}$), --

Column 48, Line 31, delete "($C_1$-$C_8$)" and insert -- ($C_1$-$C_8$) --

Column 48, Line 38, delete "($C_3$-$C_{10}$)" and insert -- ($C_3$-$C_{10}$) --

Column 48, Line 56, delete "($C_1$-$C_8$)" and insert -- ($C_1$-$C_8$) --

Column 49, Line 23, insert --$R_7$-- before "is selected....".

Signed and Sealed this

Twenty-ninth Day of June, 1999

Attest:

Q. TODD DICKINSON

*Attesting Officer*     Acting Commissioner of Patents and Trademarks